(12) United States Patent
Reed et al.

(10) Patent No.: US 7,704,700 B2
(45) Date of Patent: Apr. 27, 2010

(54) METHODS FOR DETERMINING THE PROGNOSIS FOR PATIENTS WITH A PROSTATE NEOPLASTIC CONDITION USING INHIBITOR OF APOPTOSIS POLYPEPTIDES

(75) Inventors: John C. Reed, Rancho Santa Fe, CA (US); Stan Krajewski, Oceanside, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 1948 days.

(21) Appl. No.: 10/366,307

(22) Filed: Feb. 12, 2003

(65) Prior Publication Data

US 2003/0224399 A1   Dec. 4, 2003

Related U.S. Application Data

(60) Provisional application No. 60/356,956, filed on Feb. 12, 2002.

(51) Int. Cl.
*G01N 33/574* (2006.01)
*G01N 33/53* (2006.01)

(52) U.S. Cl. .................................. 435/7.23; 435/7.1
(58) Field of Classification Search .................. 435/7.1
See application file for complete search history.

(56) References Cited

U.S. PATENT DOCUMENTS

| 4,376,110 | A |   | 3/1983  | David et al.             |
|-----------|---|---|---------|--------------------------|
| 4,778,751 | A |   | 10/1988 | Shami et al.             |
| 5,919,912 | A | * | 7/1999  | Korneluk et al. ... 530/389.2 |
| 6,107,041 | A |   | 8/2000  | Korneluk et al.          |
| 6,133,437 | A |   | 10/2000 | Korneluk et al.          |

OTHER PUBLICATIONS

Ferrieria et al (Clinical Cancer Research, 2001, 7:2468-2474).*
Liu et al (European J of Cancer, 2001, 37:1104-1110).*
Tockman et al (Cancer Res., 1992, 52:2711s-2718s).*
Slamon et al. (Science vol. 235, Jan. 1987, pp. 177-182).*
Deveraux et al., "IAP family proteins—suppressors of apoptosis", *Genes and Dev.*; 13:239-252 (1999).

Ferreira et al., "Expression of X-linked inhibitor of apoptosis as a novel prognostic marker in radically resected non-small cell lung cancer patients", *Clin. Cancer Res.*; 7:2468-2474 (2001).
Liu et al., "Anti-apoptotic proteins, apoptotic and proliferative parameters and their prognostic significance in cervical carcinoma", *Eur. J. Cancer*; 37:1104-1110 (2001).
Roy et al., "The c-IAP-1 and c-IAP-2 proteins are direct inhibitors of specific caspases", *EMBO. J.*; 16:6914-6925 (1997).
Tamm et al., "Expression and prognostic significance of IAP-family genes in human cancers and myeloid leukemias", *Clinical Cancer Res.*; 6:1796-1803 (2000).
Ambrosini et al., "A novel anti-apoptosis gene, *survivin*, expressed in cancer and lymphoma," *Nat. Med.* 3:917-921 (1997).
Deveraux et al., "X-linked IAP is a direct inhibitor of cell-death proteases," *Nature* 388:300-304 (1997).
Deveraux et al., "Cleavage of human inhibitor of apoptosis protein XIAP results in fragments with distinct specificities for caspases," *EMBO J.* 18:5242-5251 (1999).
Kato et al, "Expression of surviving in eshophageal cancer: correlation with the prognosis and response to chemotherapy," *Int. J. Cancer (Pred. Oncol.)* 95:92-95 (2001).
LaCasse et al., "The inhibitors of apoptosis (IAPs) and their emerging role in cancer," *Oncogene* 17:3247-3259 (1998).
McCarthy et al., "Apoptosis induced by *drosophila* reaper and grim in a human system," *J. Biol. Chem.* 273: 24009-24015 (1998).
Mesri et al., "Cancer gene therapy using a survivin mutant adenovirus," *J. Clin. Invest.* 108:981-990 (2001).
Paradiso et al., Expression of apoptosis-related markers and clinical outcome in patients with advanced colorectal cancer, *Br. J. Cancer* 84:651-658 (2001).
Phillips et al., "The consequences of chromosal aneuploidy on gene expression profiles in a cell line model for prostate carcinogenesis," *Cancer Res.* 61:8143-8149 (2001).
Suzuki et al., "X-Linked inhibitor of apoptosis protein (XIAP) inhibits caspase-3 and -7 in distinct modes," *J. Biol Chem.* 276:27058-27063 (2001).
Yang et al., "Ubiquitin protein ligase activity of IAPs and their degradation in proteasomes in response to apoptotic stimuli," *Science* 288:874-877 (2000).

* cited by examiner

*Primary Examiner*—Laura B Goddard
(74) *Attorney, Agent, or Firm*—McDermott Will & Emery LLP

(57) ABSTRACT

The invention provides a method of determining a prognosis for survival for a patient with a prostate neoplastic condition. The method consists of (a) measuring the level of XIAP in a neoplastic prostate cell-containing sample from the patient, and (b) comparing the level of XIAP in the sample to a reference level of XIAP, where an increased level of XIAP in the sample correlates with increased survival of the patient.

18 Claims, 9 Drawing Sheets

FIGURE 4

SEQ ID NO:1 human XIAP DNA sequence (accession no. U45880):

```
   1    gaaaaggtgg acaagtccta ttttcaagag aagatgactt taacagttt tgaaggatct
  61    aaaacttgtg tacctgcaga catcaataag gaagaagaat ttgtagaaga gtttaataga
 121    ttaaaaactt ttgctaattt tccaagtggt agtcctgttt cagcatcaac actggcacga
 181    gcagggtttc tttatactgg tgaaggagat accgtgcggt gctttagttg tcatgcagct
 241    gtagatagat ggcaatatgg agactcagca gttggaagac acaggaaagt atccccaaat
 301    tgcagattta tcaacggctt ttatcttgaa aatagtgcca cgcagtctac aaattctggt
 361    atccagaatg gtcagtacaa agttgaaaac tatctgggaa gcagagatca ttttgcctta
 421    gacaggccat ctgagacaca tgcagactat cttttgagaa ctgggcaggt tgtagatata
 481    tcagacacca tatacccgag gaaccctgcc atgtattgtg aagaagctag attaaagtcc
 541    tttcagaact ggccagacta tgctcaccta accccaagag agttagcaag tgctggactc
 601    tactacacag gtattggtga ccaagtgcag tgcttttgtt gtggtggaaa actgaaaaat
 661    tgggaacctt gtgatcgtgc ctggtcagaa cacaggcgac actttcctaa ttgcttcttt
 721    gttttgggcc ggaatcttaa tattcgaagt gaatctgatg ctgtgagttc tgataggaat
 781    ttcccaaatt caacaaatct tccaagaaat ccatccatgg cagattatga agcacggatc
 841    tttacttttg ggacatggat atactcagtt aacaaggagc agcttgcaag agctggattt
 901    tatgctttag gtgaaggtga taaagtaaag tgctttcact gtggaggagg gctaactgat
 961    tggaagccca gtgaagaccc ttgggaacaa catgctaaat ggtatccagg gtgcaaatat
1021    ctgttagaac agaagggaca agaatatata aacaatattc atttaactca ttcacttgag
1081    gagtgtctgg taagaactac tgagaaaaca ccatcactaa ctagaagaat tgatgatacc
1141    atcttccaaa atcctatggt acaagaagct atacgaatgg ggttcagttt caaggacatt
1201    aagaaaataa tggaggaaaa aattcagata tctgggagca actataaatc acttgaggtt
1261    ctggttgcag atctagtgaa tgctcagaaa gacagtatgc aagatgagtc aagtcagact
1321    tcattacaga aagagattag tactgaagag cagctaaggc gcctgcaaga ggagaagctt
1381    tgcaaaatct gtatggatag aaatattgct atcgtttttg ttccttgtgg acatctagtc
1441    acttgtaaac aatgtgctga agcagttgac aagtgtccca tgtgctacac agtcattact
1501    ttcaagcaaa aaatttttat gtcttaatct aactctatag taggcatgtt atgttgttct
1561    tattaccctg attgaatgtg tgatgtgaac tgactttaag taatcaggat tgaattccat
1621    tagcatttgc taccaagtag gaaaaaaaat gtacatggca gtgtttagt tggcaatata
1681    atctttgaat ttcttgattt ttcagggtat tagctgtatt atccattttt tttactgtta
1741    tttaattgaa accatagact aagaataaga agcatcatac tataactgaa cacaatgtgt
1801    attcatagta tactgatta atttctaagt gtaagtgaat taatcatctg gatttttat
1861    tcttttcaga taggcttaac aaatggagct ttctgtatat aaatgtggag attagagtta
1921    atctccccaa tcacataatt tgttttgtgt gaaaaaggaa taaattgttc catgctggtg
1981    gaaagataga gattgttttt agaggttggt tgttgtgttt taggattctg tccatttct
2041    tgtaaaggga taaacacgga cgtgtgcgaa atatgtttgt aaagtgattt gccattgttg
2101    aaagcgtatt taatgataga atactatcga gccaacatgt actgacatgg aaagatgtca
2161    gagatatgtt aagtgtaaaa tgcaagtggc gggacactat gtatagtctg agccagatca
2221    aagtatgtat gttgttaata tgcatagaac gagagatttg gaaagatata caccaaactg
2281    ttaaatgtgg tttctcttcg gggagggggg gattggggga ggggccccag aggggttta
2341    gaggggcctt ttcactttcg actttttca ttttgttctg ttcggattt ttataagtat
2401    gtagacccg aagggtttta tgggaactaa catcagtaac ctaaccccg tgactatcct
2461    gtgctcttcc tagggagctg tgttgtttcc cacccaccac ccttccctct gaacaaatgc
2521    ctgagtgctg gggcactttg
```

Figure 4 continued

SEQ ID NO:2 human XIAP amino acid sequence (accession no. P98170):

```
  1    mtfnsfegsk  tcvpadinke  eefveefnrl  ktfanfpsgs  pvsastlara  gflytgegdt
 61    vrcfschaav  drwqygdsav  grhrkvspnc  rfingfylen  satqstnsgi  qngqykveny
121    lgsrdhfald  rpsethadyl  lrtgqvvdis  dtiyprnpam  yseearlksf  qnwpdyahlt
181    prelasagly  ytgigdqvqc  fccggklknw  epcdrawseh  rrhfpncffv  lgrnlnirse
241    sdavssdrnf  pnstnlprnp  smadyearif  tfgtwiysvn  keqlaragfy  algegdkvkc
301    fhcggqltdw  kpsedpweqh  akwypgckyl  leqkgqeyin  nihlthslee  clvrttektp
361    sltrriddti  fqnpmvqeai  rmgfsfkdik  kimeekiqis  gsnykslevl  vadlvnaqkd
421    smqdessqts  lqkeisteeq  lrrlqeeklc  kicmdrniai  vfvpcghlvt  ckqcaeavdk
481    cpmcytvitf  kqkifms
```

SEQ ID NO:3 human cIAP1 DNA sequence (accession no. NP_no. 001166):

```
   1    gaattctatg  gagtgtaatt  ttgtgtatga  attatatttt  taaaacattg  aagagttttc
  61    agaaagaagg  ctagtagagt  tgattactga  tactttatgc  taagcagtac  ttttttggta
 121    gtacaatatt  ttgttaggcg  tttctgataa  cactagaaag  gacaagtttt  atcttgtgat
 181    aaattgatta  atgtttacaa  catgactgat  aattatagct  gaatagtcct  taaatgatga
 241    acaggttatt  tagtttttaa  atgcagtgta  aaaagtgtgc  tgtggaaatt  ttatggctaa
 301    ctaagtttat  ggagaaaata  ccttcagttg  atcaagaata  atagtggtat  acaaagttag
 361    gaagaaagtc  aacatgatgc  tgcaggaaat  ggaaacaaat  acaaatgata  tttaacaaag
 421    atagagttta  cagtttttga  actttaagcc  aaattcattt  gacatcaagc  actatagcag
 481    gcacaggttc  aacaaagctt  gtgggtattg  acttccccca  aaagttgtca  gctgaagtaa
 541    tttagcccac  ttaagtaaat  actatgatga  taagctgtgt  gaacttagct  tttaaatagt
 601    gtgaccatat  gaaggtttta  attacttttg  tttattggaa  taaaatgaga  ttttttgggt
 661    tgtcatgtta  aagtgcttat  agggaaagaa  gcctgcatat  aattttttac  cttgtggcat
 721    aatcagtaat  tggtctgtta  ttcaggcttc  atagcttgta  accaaatata  aataaaaggc
 781    ataatttagg  tattctatag  ttgcttagaa  ttttgttaat  ataaatctct  gtgaaaaatc
 841    aaggagtttt  aatattttca  gaagtgcatc  cacctttcag  ggctttaagt  tagtattact
 901    caagattatg  aacaaatagc  acttaggtta  cctgaaagag  ttactacaac  cccaaagagt
 961    tgtgttctaa  gtagtatctt  ggaaattcag  agagatactc  atcctacctg  aatataaact
1021    gagataaatc  cagtaaagaa  agtgtagtaa  attctacata  agagtctatc  attgatttct
1081    tttggtggta  aaaatcttag  ttcatgtgaa  gaaatttcat  gtgaatgttt  tagctatcaa
```

Figure 4 continued

```
1141 acagcactgt cacctactca tgcacaaaac tgcctcccaa agacttttcc caggtccctc
1201 gtatcaaaac attaagagta taatggaaga tagcacgatc ttgtcagatt ggacaaacag
1261 caacaaacaa aaaatgaagt atgacttttc ctgtgaactc tacagaatgt ctacatattc
1321 aactttcccc gccggggtgc ctgtctcaga aaggagtctt gctcgtgctg gtttttatta
1381 tactggtgtg aatgacaagg tcaaatgctt ctgttgtggc ctgatgctgg ataactggaa
1441 actaggagac agtcctattc aaaagcataa acagctatat cctagctgta gctttattca
1501 gaatctggtt tcagctagtc tgggatccac ctctaagaat acgtctccaa tgagaaacag
1561 ttttgcacat tcattatctc ccaccttgga acatagtagc ttgttcagtg gttcttactc
1621 cagcctttct ccaaaccctc ttaattctag agcagttgaa gacatctctt catcgaggac
1681 taaccc ctac agttatgcaa tgagtactga agaagccaga tttcttacct accatatgtg
1741 gccattaact tttttgtcac catcagaatt ggcaagagct ggtttttatt atataggacc
1801 tggagatagg gtagcctgct ttgcctgtgg tgggaagctc agtaactggg aaccaaagga
1861 tgatgctatg tcagaacacc ggaggcattt tcccaactgt ccattttttgg aaaattctct
1921 agaaactctg aggtttagca tttcaaatct gagcatgcag acacatgcag ctcgaatgag
1981 aacatttatg tactggccat ctagtgttcc agttcagcct gagcagcttg caagtgctgg
2041 ttttttattat gtgggtcgca atgatgatgt caaatgcttt tgttgtgatg gtggcttgag
2101 gtgttgggaa tctggagatg atccatgggt agaacatgcc aagtggtttc caaggtgtga
2161 gttcttgata cgaatgaaag gccaagagtt tgttgatgag attcaaggta gatatcctca
2221 tcttcttgaa cagctgttgt caacttcaga taccactgga gaagaaaatg ctgacccacc
2281 aattattcat tttggacctg gagaaagttc ttcagaagat gctgtcatga tgaatacacc
2341 tgtggttaaa tctgccttgg aaatgggctt taatagagac ctggtgaaac aaacagttca
2401 aagtaaaatc ctgacaactg gagagaacta taaaacagtt aatgatattg tgtcagcact
2461 tctaaatgct gaagatgaaa aagagagga ggagaaggaa aaacaagctg aagaaatggc
2521 atcagatgat ttgtcattaa ttcggaagaa cagaatggct ctctttcaac aattgacatg
2581 tgtgcttcct atcctggata atctttttaaa ggccaatgta attaataaac aggaacatga
2641 tattattaaa caaaaaacac agatacccttt acaagcgaga gaactgattg ataccatttt
2701 ggttaaagga aatgctgcgg ccaacatctt caaaaactgt ctaaagaaa ttgactctac
2761 attgtataag aacttatttg tggataagaa tatgaagtat attccaacag aagatgtttc
2821 aggtctgtca ctggaagaac aattgaggag gttgcaagaa gaacgaactt gtaaagtgtg
2881 tatggacaaa gaagtttctg ttgtatttat tccttgtggt catctggtag tatgccagga
2941 atgtgcccct tctctaagaa aatgccctat ttgcagggt ataatcaagg gtactgttcg
3001 tacatttctc tcttaaagaa aaatagtcta tattttaacc tgcataaaaa ggtctttaaa
3061 atattgttga acacttgaag ccatctaaag taaaaaggga attatgagtt tttcaattag
```

Figure 4 continued

```
3121 taacattcat gttctagtct gctttggtac taataatctt gtttctgaaa agatggtatc
3181 atatatttaa tcttaatctg tttatttaca agggaagatt tatgtttggt gaactatatt
3241 agtatgtatg tgtacctaag ggagtagtgt cactgcttgt tatgcatcat ttcaggagtt
3301 actggatttg ttgttctttc agaaagcttt gaatactaaa ttatagtgta gaaaagaact
3361 ggaaaccagg aactctggag ttcatcagag ttatggtgcc gaattgtctt tggtgctttt
3421 cacttgtgtt ttaaaataag gattttctc ttatttctcc cctagtttg tgagaaacat
3481 ctcaataaag tgcttt
```

SEQ ID NO:4 human cIAP1 amino acid sequence (accession no. NP_001157):

```
1    mhktasqrlf pgpsyqniks imedstilsd wtnsnkqkmk ydfscelyrm stystfpagv
61   pvserslara gfyytgvndk vkcfccglml dnwklgdspi qkhkqlypsc sfiqnlvsas
121  lgstskntsp mrnsfahsls ptlehsslfs gsysslspnp lnsravedis ssrtnpysya
181  msteearflt yhmwpltfls pselaragfy yigpgdrvac facggklsnw epkddamseh
241  rrhfpncpfl ensletlrfs isnlsmqtha armrtfmywp ssvpvqpeql asagfyyvgr
301  nddvkcfccd gglrcwesgd dpwvehakwf prceflirmk gqefvdeiqg ryphlleqll
361  stsdttgeen adppiihfgp gesssedavm mntpvvksal emgfnrdlvk qtvqskiltt
421  genyktvndi vsallnaede kreeekekqa eemasddlsl irknrmalfq qltcvlpild
481  nllkanvink qehdiikqkt qiplqareli dtilvkgnaa anifknclke idstlyknlf
541  vdknmkyipt edvsglslee qlrrlqeert ckvcmdkevs vvfipcghlv vcqecapslr
601  kcpicrgiik gtvrtfls
```

SEQ ID NO:5 human cIAP2 DNA nucleotide sequence (accession no. NM_001165):

```
1    gaattcaaaa tgtcttcagt tgtaaatctt accattattt tacgtacctc taagaaataa
61   aagtgcttct aattaaaata tgatgtcatt aattatgaaa tacttcttga taacagaagt
121  tttaaaatag ccatcttaga atcagtgaaa tatggtaatg tattatttc ctcctttgag
181  ttaggtcttg tgcttttttt tcctggccac taaatttcac aatttccaaa agcaaaata
241  aacatattct gaatattttt gctgtgaaac acttgacagc agagctttcc accatgaaaa
301  gaagcttcat gagtcacaca ttacatcttt gggttgattg aatgccactg aaacattcta
361  gtagcctgga gaagttgacc tacctgtgga gatgcctgcc attaaatggc atcctgatgg
```

Figure 4 continued

```
 421  cttaatacac atcactcttc tgtgaagggt tttaattttc aacacagctt actctgtagc
 481  atcatgttta cattgtatgt ataaagatta tacaaggtg caattgtgta tttcttcctt
 541  aaaatgtatc agtataggat ttagaatctc catgttgaaa ctctaaatgc atagaaataa
 601  aaataataaa aaatttttca ttttggcttt tcagcctagt attaaaactg ataaaagcaa
 661  agccatgcac aaaactacct ccctagagaa aggctagtcc cttttcttcc ccattcattt
 721  cattatgaac atagtagaaa acagcatatt cttatcaaat ttgatgaaaa gcgccaacac
 781  gtttgaactg aaatacgact tgtcatgtga actgtaccga atgtctacgt attccacttt
 841  tcctgctggg gtccctgtct cagaaaggag tcttgctcgc gctggtttct attacactgg
 901  tgtgaatgac aaggtcaaat gcttctgttg tggcctgatg ctggataact ggaaaagagg
 961  agacagtcct actgaaaagc ataaaaagtt gtatcctagc tgcagattcg ttcagagtct
1021  aaattccgtt aacaacttgg aagctacctc tcagcctact tttccttctt cagtaacaaa
1081  ttccacacac tcattacttc cgggtacaga aaacagtgga tatttccgtg gctcttattc
1141  aaactctcca tcaaatcctg taaactccag agcaaatcaa gattttctg ccttgatgag
1201  aagttcctac cactgtgcaa tgaataacga aaatgccaga ttacttactt ttcagacatg
1261  gccattgact tttctgtcgc caacagatct ggcaaaagca ggcttttact acataggacc
1321  tggagacaga gtggcttgct ttgcctgtgg tggaaaattg agcaattggg aaccgaagga
1381  taatgctatg tcagaacacc tgagacattt tcccaaatgc ccatttatag aaaatcagct
1441  tcaagacact tcaagataca cagtttctaa tctgagcatg cagacacatg cagcccgctt
1501  taaaacattc tttaactggc cctctagtgt tctagttaat cctgagcagc ttgcaagtgc
1561  gggtttttat tatgtgggta acagtgatga tgtcaaatgc ttttgctgtg atggtggact
1621  caggtgttgg gaatctggag atgatccatg ggttcaacat gccaagtggt ttccaaggtg
1681  tgagtacttg ataagaatta aggacagga gttcatccgt caagttcaag ccagttaccc
1741  tcatctactt gaacagctgc tatccacatc agacagccca ggagatgaaa atgcagagtc
1801  atcaattatc catttgaac ctggagaaga ccattcagaa gatgcaatca tgatgaatac
1861  tcctgtgatt aatgctgccg tggaaatggg ctttagtaga agcctggtaa aacagacagt
1921  tcagagaaaa atcctagcaa ctggagagaa ttatagacta gtcaatgatc ttgtgttaga
1981  cttactcaat gcagaagatg aaataaggga agaggagaga gaaagagcaa ctgaggaaaa
2041  agaatcaaat gatttattat taatccggaa gaatagaatg gcacttttc aacatttgac
2101  ttgtgtaatt ccaatcctgg atagtctact aactgccgga attattaatg aacaagaaca
2161  tgatgttatt aaacagaaga cacagacgtc tttacaagca agagaactga ttgatacgat
2221  tttagtaaaa ggaaatattg cagccactgt attcagaaac tctctgcaag aagctgaagc
2281  tgtgttatat gagcatttat ttgtgcaaca ggacataaaa tatattccca cagaagatgt
```

Figure 4 continued

```
2341 ttcagatcta ccagtggaag aacaattgcg gagactacaa gaagaaagaa catgtaaagt
2401 gtgtatggac aaagaagtgt ccatagtgtt tattccttgt ggtcatctag tagtatgcaa
2461 agattgtgct ccttctttaa gaaagtgtcc tatttgtagg agtacaatca agggtacagt
2521 tcgtacattt ctttcatgaa gaagaaccaa aacatcatct aaactttaga attaatttat
2581 taaatgtatt ataactttaa ctttcatcct aatttggttt ccttaaaatt tttatttatt
2641 tacaactcaa caaacattgt tttgtgtaac atatttaata tatgtatcta aaccatatga
2701 acatatattt tttagaaact aagagaatga taggcttttg ttcttatgaa cgaaaaagag
2761 gtagcactac aaacacaata ttcaatcaaa atttcagcat tattgaaatt gtaagtgaag
2821 taaaacttaa gatatttgag ttaacccttta agaatttaa atattttggc attgtactaa
2881 taccgggaac atgaagccag gtgtggtggt atgtgcctgt agtcccaggc tgaggcaaga
2941 gaattacttg agcccaggag tttgaatcca tcctgggcag catactgaga ccctgccttt
3001 aaaaacaaac agaacaaaaa caaaacacca gggacacatt tctctgtctt ttttgatcag
3061 tgtcctatac atcgaaggtg tgcatatatg ttgaatgaca tttagggac atggtgtttt
3121 tataaagaat tctgtgagaa aaaatttaat aaaaccccc aaatt
```

SEQ ID NO:6 human cIAP2 amino acid sequence (accession no. NP_001156):

```
1    mnivensifl snlmksantf elkydlscel yrmstystfp agvpvsersl aragfyytgv
61   ndkvkcfccg lmldnwkrgd sptekhkkly pscrfvqsln svnnleatsq ptfpssvtns
121  thsllpgten sgyfrgsysn spsnpvnsra nqdfsalmrs syhcamnnen arlltfqtwp
181  ltflsptdla kagfyyigpg drvacfacgg klsnwepkdn amsehlrhfp kcpfienqlq
241  dtsrytvsnl smqthaarfk tffnwpssvl vnpeqlasag fyyvgnsddv kcfccdggglr
301  cwesgddpwv qhakwfprce ylirikgqef irqvqasyph lleqllstsd spgdenaess
361  iihfepgedh sedaimmntp vinaavemgf srslvkqtvq rkilatgeny rlvndlvldl
421  lnaedeiree ererateeke sndlllirkn rmalfqhltc vipildsllt agiineqehd
481  vikqktqtsl qarelidtil vkgniaatvf rnslqeaeav lyehlfvqqd ikyiptedvs
541  dlpveeqlrr lqeertckvc mdkevsivfi pcghlvvckd capslrkcpi crstikgtvr
601  tfls
```

SEQUENCE LISTING

<160> NUMBER OF SEQ ID NOS: 6

<210> SEQ ID NO 1
<211> LENGTH: 2540
<212> TYPE: DNA
<213> ORGANISM: Homo sapiens

<400> SEQUENCE: 1

```
gaaaaggtgg acaagtccta ttttcaagag aagatgactt ttaacagttt tgaaggatct      60
aaaacttgtg tacctgcaga catcaataag gaagaagaat tgtagaaga gtttaataga     120
ttaaaaactt ttgctaattt tccaagtggt agtcctgttt cagcatcaac actggcacga    180
gcagggtttc tttatactgg tgaaggagat accgtgcggt gcttagttg tcatgcagct     240
gtagatagat ggcaatatgg agactcagca gttggaagac acaggaaagt atccccaaat    300
tgcagattta tcaacggctt ttatcttgaa aatagtgcca cgcagtctac aaattctggt    360
atccagaatg gtcagtacaa agttgaaaac tatctgggaa gcagagatca ttttgcctta    420
gacaggccat ctgagacaca tgcagactat cttttgagaa ctgggcaggt tgtagatata    480
tcagacacca tacccgag gaaccctgcc atgtattgtg aagaagctag attaaagtcc      540
tttcagaact ggccagacta tgctcaccta accccaagag agttagcaag tgctggactc    600
tactacacag gtattggtga ccaagtgcag tgcttttgtt gtggtggaaa actgaaaaat    660
tgggaacctt gtgatcgtgc ctggtcagaa cacaggcgac actttcctaa ttgcttcttt    720
gttttgggcc ggaatcttaa tattcgaagt gaatctgatg ctgtgagttc tgataggaat    780
ttcccaaatt caacaaatct tccaagaaat ccatccatgg cagattatga agcacggatc    840
tttacttttg ggacatggat atactcagtt aacaaggagc agcttgcaag agctggattt    900
tatgctttag gtgaaggtga taaagtaaag tgctttcact gtggaggagg gctaactgat    960
tggaagccca gtgaagaccc ttgggaacaa catgctaaat ggtatccagg gtgcaaatat    1020
ctgttagaac agaagggaca agaatatata aacaatattc atttaactca ttcacttgag    1080
gagtgtctgg taagaactac tgagaaaaca ccatcactaa ctagaagaat tgatgatacc    1140
atcttccaaa atcctatggt acaagaagct atacgaatgg ggttcagttt caaggacatt    1200
aagaaaataa tggaggaaaa aattcagata tctgggagca actataaatc acttgaggtt    1260
ctggttgcag atctagtgaa tgctcagaaa gacagtatgc aagatgagtc aagtcagact    1320
tcattacaga aagagattag tactgaagag cagctaaggc gcctgcaaga ggagaagctt    1380
tgcaaaatct gtatggatag aaatattgct atcgtttttg ttccttgtgg acatctagtc    1440
acttgtaaac aatgtgctga agcagttgac aagtgtccca tgtgctacac agtcattact    1500
ttcaagcaaa aaattttat gtcttaatct aactctatag taggcatgtt atgttgttct    1560
tattaccctg attgaatgtg tgatgtgaac tgacttaag taatcaggat tgaattccat      1620
tagcatttgc taccaagtag gaaaaaaaat gtacatggca gtgttttagt tggcaatata    1680
atctttgaat tcttgatttt tcagggtat tagctgtatt atccattttt tttactgtta     1740
tttaattgaa accatagact aagaataaga agcatcatac tataactgaa cacaatgtgt    1800
attcatagta tactgattta atttctaagt gtaagtgaat taatcatctg gattttttat    1860
tcttttcaga taggcttaac aaatggagct ttctgtatat aaatgtggag attagagtta    1920
atctccccaa tcacataatt tgttttgtgt gaaaaggaa taaattgttc catgctggtg     1980
gaaagataga gattgttttt agaggttggt tgttgtgttt taggattctg tccatttctct   2040
```

-continued

```
tgtaaaggga taaacacgga cgtgtgcgaa atatgtttgt aaagtgattt gccattgttg    2100
aaagcgtatt taatgataga atactatcga gccaacatgt actgacatgg aaagatgtca    2160
gagatatgtt aagtgtaaaa tgcaagtggc gggacactat gtatagtctg agccagatca    2220
aagtatgtat gttgttaata tgcatagaac gagagatttg gaaagatata caccaaactg    2280
ttaaatgtgg tttctcttcg ggagggggg gattggggga ggggcccag aggggtttta     2340 gaggggcctt ttcactttcg acttttttca ttttgttctg ttcggatttt ttataagtat    2400
gtagaccccg aagggtttta tgggaactaa catcagtaac ctaaccccg tgactatcct     2460 gtgctcttcc tagggagctg tgttgtttcc cacccaccac ccttccctct gaacaaatgc    2520
ctgagtgctg gggcactttg                                                2540
```

<210> SEQ ID NO 2
<211> LENGTH: 497
<212> TYPE: PRT
<213> ORGANISM: Homo sapiens

<400> SEQUENCE: 2

```
Met Thr Phe Asn Ser Phe Glu Gly Ser Lys Thr Cys Val Pro Ala Asp
  1               5                  10                  15

Ile Asn Lys Glu Glu Glu Phe Val Glu Phe Asn Arg Leu Lys Thr
             20                  25                  30

Phe Ala Asn Phe Pro Ser Gly Ser Pro Val Ser Ala Ser Thr Leu Ala
         35                  40                  45

Arg Ala Gly Phe Leu Tyr Thr Gly Glu Gly Asp Thr Val Arg Cys Phe
     50                  55                  60

Ser Cys His Ala Ala Val Asp Arg Trp Gln Tyr Gly Asp Ser Ala Val
 65                  70                  75                  80

Gly Arg His Arg Lys Val Ser Pro Asn Cys Arg Phe Ile Asn Gly Phe
                 85                  90                  95

Tyr Leu Glu Asn Ser Ala Thr Gln Ser Thr Asn Ser Gly Ile Gln Asn
            100                 105                 110

Gly Gln Tyr Lys Val Glu Asn Tyr Leu Gly Ser Arg Asp His Phe Ala
        115                 120                 125

Leu Asp Arg Pro Ser Glu Thr His Ala Asp Tyr Leu Leu Arg Thr Gly
    130                 135                 140

Gln Val Val Asp Ile Ser Asp Thr Ile Tyr Pro Arg Asn Pro Ala Met
145                 150                 155                 160

Tyr Ser Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ile Gly Asp Gln Val Gln Cys Phe Cys Cys Gly Gly Lys Leu Lys
        195                 200                 205

Asn Trp Glu Pro Cys Asp Arg Ala Trp Ser Glu His Arg Arg His Phe
    210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
            260                 265                 270

Gly Thr Trp Ile Tyr Ser Val Asn Lys Glu Gln Leu Ala Arg Ala Gly
```

-continued

```
                275                 280                 285
Phe Tyr Ala Leu Gly Glu Gly Asp Lys Val Lys Cys Phe His Cys Gly
        290                 295                 300
Gly Gly Leu Thr Asp Trp Lys Pro Ser Glu Asp Pro Trp Glu Gln His
305                 310                 315                 320
Ala Lys Trp Tyr Pro Gly Cys Lys Tyr Leu Leu Glu Gln Lys Gly Gln
                325                 330                 335
Glu Tyr Ile Asn Asn Ile His Leu Thr His Ser Leu Glu Glu Cys Leu
            340                 345                 350
Val Arg Thr Thr Glu Lys Thr Pro Ser Leu Thr Arg Arg Ile Asp Asp
        355                 360                 365
Thr Ile Phe Gln Asn Pro Met Val Gln Glu Ala Ile Arg Met Gly Phe
    370                 375                 380
Ser Phe Lys Asp Ile Lys Lys Ile Met Glu Glu Lys Ile Gln Ile Ser
385                 390                 395                 400
Gly Ser Asn Tyr Lys Ser Leu Glu Val Leu Val Ala Asp Leu Val Asn
                405                 410                 415
Ala Gln Lys Asp Ser Met Gln Asp Glu Ser Ser Gln Thr Ser Leu Gln
            420                 425                 430
Lys Glu Ile Ser Thr Glu Gln Leu Arg Arg Leu Gln Glu Glu Lys
        435                 440                 445
Leu Cys Lys Ile Cys Met Asp Arg Asn Ile Ala Ile Val Phe Val Pro
    450                 455                 460
Cys Gly His Leu Val Thr Cys Lys Gln Cys Ala Glu Ala Val Asp Lys
465                 470                 475                 480
Cys Pro Met Cys Tyr Thr Val Ile Thr Phe Lys Gln Lys Ile Phe Met
                485                 490                 495
Ser
```

<210> SEQ ID NO 3
<211> LENGTH: 3496
<212> TYPE: DNA
<213> ORGANISM: Homo sapiens

<400> SEQUENCE: 3

```
gaattctatg gagtgtaatt ttgtgtatga attatatttt taaaacattg aagagttttc    60
agaaagaagg ctagtagagt tgattactga tactttatgc taagcagtac tttttttggta   120
gtacaatatt ttgttaggcg tttctgataa cactagaaag acaagttttt atcttgtgat   180
aaattgatta atgtttacaa catgactgat aattatagct gaatagtcct taaatgatga   240
acaggttatt tagttttttaa atgcagtgta aaaagtgtgc tgtggaaatt ttatggctaa   300
ctaagtttat ggagaaaata ccttcagttg atcaagaata atagtggtat acaaagttag   360
gaagaaagtc aacatgatgc tgcaggaaat ggaaacaaat acaaatgata tttaacaaag   420
atagagttta cagttttttga actttaagcc aaattcattt gacatcaagc actatagcag   480
gcacaggttc aacaaagctt gtgggtattg acttccccca aaagttgtca gctgaagtaa   540
tttagcccac ttaagtaaat actatgatga taagctgtgt gaacttagct tttaaatagt   600
gtgaccatat gaaggtttta attactttttg tttattggaa taaatgaga ttttttgggt    660
tgtcatgtta aagtgcttat agggaaagaa gcctgcatat aatttttttac cttgtggcat   720
aatcagtaat tggtctgtta ttcaggcttc atagcttgta accaaatata aataaaaggc   780
ataatttagg tattctatag ttgcttagaa ttttgttaat ataaatctct gtgaaaaatc   840
```

```
aaggagtttt aatattttca gaagtgcatc caccttttcag ggctttaagt tagtattact    900
caagattatg aacaaatagc acttaggtta cctgaaagag ttactacaac cccaaagagt    960
tgtgttctaa gtagtatctt ggaaattcag agagatactc atcctacctg aatataaact   1020
gagataaatc cagtaaagaa agtgtagtaa attctacata agagtctatc attgatttct   1080
tttggtggta aaaatcttag ttcatgtgaa gaaatttcat gtgaatgttt tagctatcaa   1140
acagcactgt cacctactca tgcacaaaac tgcctcccaa agacttttcc caggtccctc   1200
gtatcaaaac attaagagta taatggaaga tagcacgatc ttgtcagatt ggacaaacag   1260
caacaaacaa aaaatgaagt atgacttttc ctgtgaactc tacagaatgt ctacatattc   1320
aactttcccc gccggggtgc ctgtctcaga aggagtctt gctcgtgctg gtttttatta   1380
tactggtgtg aatgacaagg tcaaatgctt ctgttgtggc ctgatgctgg ataactggaa   1440
actaggagac agtcctattc aaaagcataa acagctatat cctagctgta gctttattca   1500
gaatctggtt tcagctagtc tgggatccac ctctaagaat acgtctccaa tgagaaacag   1560
ttttgcacat tcattatctc ccaccttgga acatagtagc ttgttcagtg gttcttactc   1620
cagccttttct ccaaaccctc ttaattctag agcagttgaa gacatctctt catcgaggac   1680
taacccctac agttatgcaa tgagtactga agaagccaga tttcttacct accatatgtg   1740
gccattaact tttttgtcac catcagaatt ggcaagagct ggttttttatt atataggacc   1800
tggagatagg gtagcctgct tgcctgtggg tgggaagctc agtaactggg aaccaaagga   1860
tgatgctatg tcagaacacc ggaggcattt tcccaactgt ccattttttgg aaaattctct   1920
agaaactctg aggtttagca tttcaaatct gagcatgcag acacatgcag ctcgaatgag   1980
aacatttatg tactgccat ctagtgttcc agttcagcct gagcagcttg caagtgctgg   2040
ttttttattat gtgggtcgca atgatgatgt caaatgcttt tgttgtgatg gtggcttgag   2100
gtgttgggaa tctggagatg atccatgggt agaacatgcc aagtggtttc caaggtgtga   2160
gttcttgata cgaatgaaag gccaagagtt tgttgatgag attcaaggta gatatcctca   2220
tcttcttgaa cagctgttgt caacttcaga taccactgga gaagaaaatg ctgacccacc   2280
aattattcat tttggacctg agaaaagttc ttcagaagat gctgtcatga tgaatacacc   2340
tgtggttaaa tctgccttgg aaatgggctt aatagagac ctggtgaaac aaacagttca   2400
aagtaaaatc ctgacaactg gagagaacta taaaacagtt aatgatattg tgtcagcact   2460
tctaaatgct gaagatgaaa aagagagga ggagaaggaa aaacaagctg aagaaatggc   2520
atcagatgat ttgtcattaa ttcggaagaa cagaatggct ctctttcaac aattgacatg   2580
tgtgcttcct atcctggata atcttttaaa ggccaatgta attaataaac aggaacatga   2640
tattattaaa caaaaaacac agatacccttt acaagcgaga gaactgattg ataccatttt   2700
ggttaaagga aatgctgcgg ccaacatctt caaaaactgt ctaaaagaaa ttgactctac   2760
attgtataag aacttatttg tggataagaa tatgaagtat attccaacag aagatgtttc   2820
aggtctgtca ctggaagaac aattgaggag gttgcaagaa gaacgaactt gtaaagtgtg   2880
tatgacaaaa gaagtttctg ttgtatttat tccttgtggt catctggtag tatgccagga   2940
atgtgcccct tctctaagaa aatgccctat ttgcagggt ataatcaagg gtactgttcg   3000
tacatttctc tcttaaagaa aaatagtcta tatttttaacc tgcataaaaa ggtctttaaa   3060
atattgttga acacttgaag ccatctaaag taaaaggga attatgagtt tttcaattag   3120
taacattcat gttctagtct gctttggtac taataatctt gtttctgaaa agatggtatc   3180
atatatttaa tcttaatctg tttatttaca agggaagatt tatgtttggt gaactatatt   3240
```

-continued

```
agtatgtatg tgtacctaag ggagtagtgt cactgcttgt tatgcatcat ttcaggagtt    3300
actggatttg ttgttctttc agaaagcttt gaatactaaa ttatagtgta gaaagaact    3360 ggaaaccagg aactctggag ttcatcagag ttatggtgcc gaattgtctt tggtgctttt    3420
cacttgtgtt ttaaaataag gattttctc ttatttctcc ccctagtttg tgagaaacat    3480
ctcaataaag tgcttt    3496
```

<210> SEQ ID NO 4
<211> LENGTH: 618
<212> TYPE: PRT
<213> ORGANISM: Homo sapiens

<400> SEQUENCE: 4

```
Met His Lys Thr Ala Ser Gln Arg Leu Phe Pro Gly Pro Ser Tyr Gln
 1               5                   10                  15

Asn Ile Lys Ser Ile Met Glu Asp Ser Thr Ile Leu Ser Asp Trp Thr
             20                  25                  30

Asn Ser Asn Lys Gln Lys Met Lys Tyr Asp Phe Ser Cys Glu Leu Tyr
         35                  40                  45

Arg Met Ser Thr Tyr Ser Thr Phe Pro Ala Gly Val Pro Val Ser Glu
     50                  55                  60

Arg Ser Leu Ala Arg Ala Gly Phe Tyr Tyr Thr Gly Val Asn Asp Lys
 65                  70                  75                  80

Val Lys Cys Phe Cys Cys Gly Leu Met Leu Asp Asn Trp Lys Leu Gly
                 85                  90                  95

Asp Ser Pro Ile Gln Lys His Lys Gln Leu Tyr Pro Ser Cys Ser Phe
            100                 105                 110

Ile Gln Asn Leu Val Ser Ala Ser Leu Gly Ser Thr Ser Lys Asn Thr
        115                 120                 125

Ser Pro Met Arg Asn Ser Phe Ala His Ser Leu Ser Pro Thr Leu Glu
    130                 135                 140

His Ser Ser Leu Phe Ser Gly Ser Tyr Ser Ser Leu Ser Pro Asn Pro
145                 150                 155                 160

Leu Asn Ser Arg Ala Val Glu Asp Ile Ser Ser Ser Arg Thr Asn Pro
                165                 170                 175

Tyr Ser Tyr Ala Met Ser Thr Glu Glu Ala Arg Phe Leu Thr Tyr His
            180                 185                 190

Met Trp Pro Leu Thr Phe Leu Ser Pro Ser Glu Leu Ala Arg Ala Gly
        195                 200                 205

Phe Tyr Tyr Ile Gly Pro Gly Asp Arg Val Ala Cys Phe Ala Cys Gly
    210                 215                 220

Gly Lys Leu Ser Asn Trp Glu Pro Lys Asp Asp Ala Met Ser Glu His
225                 230                 235                 240

Arg Arg His Phe Pro Asn Cys Pro Phe Leu Glu Asn Ser Leu Glu Thr
                245                 250                 255

Leu Arg Phe Ser Ile Ser Asn Leu Ser Met Gln Thr His Ala Ala Arg
            260                 265                 270

Met Arg Thr Phe Met Tyr Trp Pro Ser Ser Val Pro Val Gln Pro Glu
        275                 280                 285

Gln Leu Ala Ser Ala Gly Phe Tyr Tyr Val Gly Arg Asn Asp Asp Val
    290                 295                 300

Lys Cys Phe Cys Cys Asp Gly Gly Leu Arg Cys Trp Glu Ser Gly Asp
305                 310                 315                 320
```

```
Asp Pro Trp Val Glu His Ala Lys Trp Phe Pro Arg Cys Glu Phe Leu
                325                 330                 335
Ile Arg Met Lys Gly Gln Glu Phe Val Asp Glu Ile Gln Gly Arg Tyr
            340                 345                 350
Pro His Leu Leu Glu Gln Leu Leu Ser Thr Ser Asp Thr Thr Gly Glu
        355                 360                 365
Glu Asn Ala Asp Pro Pro Ile Ile His Phe Gly Pro Gly Glu Ser Ser
    370                 375                 380
Ser Glu Asp Ala Val Met Met Asn Thr Pro Val Val Lys Ser Ala Leu
385                 390                 395                 400
Glu Met Gly Phe Asn Arg Asp Leu Val Lys Gln Thr Val Gln Ser Lys
                405                 410                 415
Ile Leu Thr Thr Gly Glu Asn Tyr Lys Thr Val Asn Asp Ile Val Ser
            420                 425                 430
Ala Leu Leu Asn Ala Glu Asp Glu Lys Arg Glu Glu Lys Glu Lys
        435                 440                 445
Gln Ala Glu Glu Met Ala Ser Asp Asp Leu Ser Leu Ile Arg Lys Asn
    450                 455                 460
Arg Met Ala Leu Phe Gln Gln Leu Thr Cys Val Leu Pro Ile Leu Asp
465                 470                 475                 480
Asn Leu Leu Lys Ala Asn Val Ile Asn Lys Gln Glu His Asp Ile Ile
                485                 490                 495
Lys Gln Lys Thr Gln Ile Pro Leu Gln Ala Arg Glu Leu Ile Asp Thr
            500                 505                 510
Ile Leu Val Lys Gly Asn Ala Ala Ala Asn Ile Phe Lys Asn Cys Leu
        515                 520                 525
Lys Glu Ile Asp Ser Thr Leu Tyr Lys Asn Leu Phe Val Asp Lys Asn
    530                 535                 540
Met Lys Tyr Ile Pro Thr Glu Asp Val Ser Gly Leu Ser Leu Glu Glu
545                 550                 555                 560
Gln Leu Arg Arg Leu Gln Glu Glu Arg Thr Cys Lys Val Cys Met Asp
                565                 570                 575
Lys Glu Val Ser Val Val Phe Ile Pro Cys Gly His Leu Val Val Cys
            580                 585                 590
Gln Glu Cys Ala Pro Ser Leu Arg Lys Cys Pro Ile Cys Arg Gly Ile
        595                 600                 605
Ile Lys Gly Thr Val Arg Thr Phe Leu Ser
    610                 615

<210> SEQ ID NO 5
<211> LENGTH: 3165
<212> TYPE: DNA
<213> ORGANISM: Homo sapiens

<400> SEQUENCE: 5
gaattcaaaa tgtcttcagt tgtaaatctt accattattt tacgtacctc taagaaataa      60
aagtgcttct aattaaaata tgatgtcatt aattatgaaa tacttcttga taacagaagt     120
tttaaaatag ccatcttaga atcagtgaaa tatggtaatg tattattttc ctcctttgag     180
ttaggtcttg tgcttttttt tcctggccac taaatttcac aatttccaaa agcaaaata      240 aacatattct gaatattttt gctgtgaaac acttgacagc agagctttcc accatgaaaa     300
gaagcttcat gagtcacaca ttacatcttt gggttgattg aatgccactg aaacattcta     360
gtagcctgga gaagttgacc tacctgtgga gatgcctgcc attaaatggc atcctgatgg     420
```

| | |
|---|---|
| cttaatacac atcactcttc tgtgaagggt tttaattttc aacacagctt actctgtagc | 480 |
| atcatgttta cattgtatgt ataaagatta tacaaaggtg caattgtgta tttcttcctt | 540 |
| aaaatgtatc agtataggat ttagaatctc catgttgaaa ctctaaatgc atagaaataa | 600 |
| aaataataaa aaattttca ttttggcttt tcagcctagt attaaaactg ataaaagcaa | 660 |
| agccatgcac aaaactacct ccctagagaa aggctagtcc cttttcttcc ccattcattt | 720 |
| cattatgaac atagtagaaa acagcatatt cttatcaaat ttgatgaaaa gcgccaacac | 780 |
| gtttgaactg aaatacgact tgtcatgtga actgtaccga atgtctacgt attccacttt | 840 |
| tcctgctggg gtccctgtct cagaaaggag tcttgctcgc gctggtttct attacactgg | 900 |
| tgtgaatgac aaggtcaaat gcttctgttg tggcctgatg ctggataact ggaaaagagg | 960 |
| agacagtcct actgaaaagc ataaaaagtt gtatcctagc tgcagattcg ttcagagtct | 1020 |
| aaattccgtt aacaacttgg aagctacctc tcagcctact tttccttctt cagtaacaaa | 1080 |
| ttccacacac tcattacttc cgggtacaga aaacagtgga tatttccgtg gctcttattc | 1140 |
| aaactctcca tcaaatcctg taaactccag agcaaatcaa gattttctg ccttgatgag | 1200 |
| aagttcctac cactgtgcaa tgaataacga aaatgccaga ttacttactt ttcagacatg | 1260 |
| gccattgact tttctgtcgc aacagatct ggcaaaagca ggctttact acataggacc | 1320 |
| tggagacaga gtggcttgct ttgcctgtgg tggaaaattg agcaattggg aaccgaagga | 1380 |
| taatgctatg tcagaacacc tgagacattt tcccaaatgc ccatttatag aaaatcagct | 1440 |
| tcaagacact tcaagataca cagtttctaa tctgagcatg cagacacatg cagcccgctt | 1500 |
| taaaacattc tttaactggc cctctagtgt tctagttaat cctgagcagc ttgcaagtgc | 1560 |
| gggtttttat tatgtgggta acagtgatga tgtcaaatgc ttttgctgtg atggtggact | 1620 |
| caggtgttgg gaatctggag atgatccatg ggttcaacat gccaagtggt ttccaaggtg | 1680 |
| tgagtacttg ataagaatta aaggacagga gttcatccgt caagttcaag ccagttaccc | 1740 |
| tcatctactt gaacagctgc tatccacatc agacagccca ggagatgaaa atgcagagtc | 1800 |
| atcaattatc cattttgaac ctggagaaga ccattcagaa gatgcaatca tgatgaatac | 1860 |
| tcctgtgatt aatgctgccg tggaaatggg ctttagtaga agcctggtaa acagacagt | 1920 |
| tcagagaaaa atcctagcaa ctggagagaa ttatagacta gtcaatgatc ttgtgttaga | 1980 |
| cttactcaat gcagaagatg aaataaggga agaggagaga gaaagagcaa ctgaggaaaa | 2040 |
| agaatcaaat gatttattat taatccggaa gaatagaatg gcacttttc aacatttgac | 2100 |
| ttgtgtaatt ccaatcctgg atagtctact aactgccgga attattaatg aacaagaaca | 2160 |
| tgatgttatt aaacagaaga cacagacgtc tttacaagca agagaactga ttgatacgat | 2220 |
| tttagtaaaa ggaaatattg cagccactgt attcagaaac tctctgcaag aagctgaagc | 2280 |
| tgtgttatat gagcatttat ttgtgcaaca ggacataaaa tatattccca cagaagatgt | 2340 |
| ttcagatcta ccagtggaag aacaattgcg gagactacaa gaagaaagaa catgtaaagt | 2400 |
| gtgtatggac aaagaagtgt ccatagtgtt tattccttgt ggtcatctag tagtatgcaa | 2460 |
| agattgtgct ccttctttaa gaaagtgtcc tatttgtagg agtacaatca agggtacagt | 2520 |
| tcgtacattt ctttcatgaa gaagaaccaa acatcatct aaactttaga attaatttat | 2580 |
| taaatgtatt ataactttaa ctttcatcct aatttggttt ccttaaaatt tttatttatt | 2640 |
| tacaactcaa caaacattgt tttgtgtaac atatttaata tatgtatcta aaccatatga | 2700 |
| acatatattt tttagaaact aagagaatga taggcttttg ttcttatgaa cgaaaaagag | 2760 |
| gtagcactac aaacacaata ttcaatcaaa atttcagcat tattgaaatt gtaagtgaag | 2820 |

```
taaaacttaa gatatttgag ttaacccttta agaattttaa atattttggc attgtactaa    2880
taccgggaac atgaagccag gtgtggtggt atgtgcctgt agtcccaggc tgaggcaaga    2940
gaattacttg agcccaggag tttgaatcca tcctgggcag catactgaga ccctgccttt    3000
aaaaacaaac agaacaaaaa caaaacacca gggacacatt tctctgtctt ttttgatcag    3060
tgtcctatac atcgaaggtg tgcatatatg ttgaatgaca ttttagggac atggtgtttt    3120
tataaagaat tctgtgagaa aaaatttaat aaaaccccccc aaatt                  3165
```

```
<210> SEQ ID NO 6
<211> LENGTH: 604
<212> TYPE: PRT
<213> ORGANISM: Homo sapiens

<400> SEQUENCE: 6

Met Asn Ile Val Glu Asn Ser Ile Phe Leu Ser Asn Leu Met Lys Ser
 1               5                  10                  15

Ala Asn Thr Phe Glu Leu Lys Tyr Asp Leu Ser Cys Glu Leu Tyr Arg
                20                  25                  30

Met Ser Thr Tyr Ser Thr Phe Pro Ala Gly Val Pro Val Ser Glu Arg
            35                  40                  45

Ser Leu Ala Arg Ala Gly Phe Tyr Tyr Thr Gly Val Asn Asp Lys Val
        50                  55                  60

Lys Cys Phe Cys Cys Gly Leu Met Leu Asp Asn Trp Lys Arg Gly Asp
65                  70                  75                  80

Ser Pro Thr Glu Lys His Lys Lys Leu Tyr Pro Ser Cys Arg Phe Val
                85                  90                  95

Gln Ser Leu Asn Ser Val Asn Asn Leu Glu Ala Thr Ser Gln Pro Thr
            100                 105                 110

Phe Pro Ser Ser Val Thr Asn Ser Thr His Ser Leu Leu Pro Gly Thr
        115                 120                 125

Glu Asn Ser Gly Tyr Phe Arg Gly Ser Tyr Ser Asn Ser Pro Ser Asn
    130                 135                 140

Pro Val Asn Ser Arg Ala Asn Gln Asp Phe Ser Ala Leu Met Arg Ser
145                 150                 155                 160

Ser Tyr His Cys Ala Met Asn Asn Glu Asn Ala Arg Leu Leu Thr Phe
                165                 170                 175

Gln Thr Trp Pro Leu Thr Phe Leu Ser Pro Thr Asp Leu Ala Lys Ala
            180                 185                 190

Gly Phe Tyr Tyr Ile Gly Pro Gly Asp Arg Val Ala Cys Phe Ala Cys
        195                 200                 205

Gly Gly Lys Leu Ser Asn Trp Glu Pro Lys Asp Asn Ala Met Ser Glu
    210                 215                 220

His Leu Arg His Phe Pro Lys Cys Pro Phe Ile Glu Asn Gln Leu Gln
225                 230                 235                 240

Asp Thr Ser Arg Tyr Thr Val Ser Asn Leu Ser Met Gln Thr His Ala
                245                 250                 255

Ala Arg Phe Lys Thr Phe Phe Asn Trp Pro Ser Ser Val Leu Val Asn
            260                 265                 270

Pro Glu Gln Leu Ala Ser Ala Gly Phe Tyr Tyr Val Gly Asn Ser Asp
        275                 280                 285

Asp Val Lys Cys Phe Cys Cys Asp Gly Gly Leu Arg Cys Trp Glu Ser
    290                 295                 300

Gly Asp Asp Pro Trp Val Gln His Ala Lys Trp Phe Pro Arg Cys Glu
```

-continued

```
305                 310                 315                 320
Tyr Leu Ile Arg Ile Lys Gly Gln Glu Phe Ile Arg Gln Val Gln Ala
                325                 330                 335

Ser Tyr Pro His Leu Leu Glu Gln Leu Leu Ser Thr Ser Asp Ser Pro
            340                 345                 350

Gly Asp Glu Asn Ala Glu Ser Ser Ile Ile His Phe Glu Pro Gly Glu
            355                 360                 365

Asp His Ser Glu Asp Ala Ile Met Met Asn Thr Pro Val Ile Asn Ala
        370                 375                 380

Ala Val Glu Met Gly Phe Ser Arg Ser Leu Val Lys Gln Thr Val Gln
385                 390                 395                 400

Arg Lys Ile Leu Ala Thr Gly Glu Asn Tyr Arg Leu Val Asn Asp Leu
                405                 410                 415

Val Leu Asp Leu Leu Asn Ala Glu Asp Glu Ile Arg Glu Glu Glu Arg
            420                 425                 430

Glu Arg Ala Thr Glu Glu Lys Glu Ser Asn Asp Leu Leu Leu Ile Arg
            435                 440                 445

Lys Asn Arg Met Ala Leu Phe Gln His Leu Thr Cys Val Ile Pro Ile
    450                 455                 460

Leu Asp Ser Leu Leu Thr Ala Gly Ile Ile Asn Glu Gln Glu His Asp
465                 470                 475                 480

Val Ile Lys Gln Lys Thr Gln Thr Ser Leu Gln Ala Arg Glu Leu Ile
                485                 490                 495

Asp Thr Ile Leu Val Lys Gly Asn Ile Ala Ala Thr Val Phe Arg Asn
            500                 505                 510

Ser Leu Gln Glu Ala Glu Ala Val Leu Tyr Glu His Leu Phe Val Gln
            515                 520                 525

Gln Asp Ile Lys Tyr Ile Pro Thr Glu Asp Val Ser Asp Leu Pro Val
        530                 535                 540

Glu Glu Gln Leu Arg Arg Leu Gln Glu Glu Arg Thr Cys Lys Val Cys
545                 550                 555                 560

Met Asp Lys Glu Val Ser Ile Val Phe Ile Pro Cys Gly His Leu Val
                565                 570                 575

Val Cys Lys Asp Cys Ala Pro Ser Leu Arg Lys Cys Pro Ile Cys Arg
            580                 585                 590

Ser Thr Ile Lys Gly Thr Val Arg Thr Phe Leu Ser
            595                 600
```

1

METHODS FOR DETERMINING THE PROGNOSIS FOR PATIENTS WITH A PROSTATE NEOPLASTIC CONDITION USING INHIBITOR OF APOPTOSIS POLYPEPTIDES

This application claims benefit of the filing date of U.S. Provisional Application No. 60/356,956, filed Feb. 12, 2002, and which is incorporated herein by reference.

The present invention relates generally to regulation of programmed cell death and more specifically to biomarkers for predicting survival of patients with a prostate neoplastic condition.

BACKGROUND OF THE INVENTION

Prognosis in clinical cancer is an area of great concern and interest. It is important to know the aggressiveness of the malignant cells and the likelihood of tumor recurrence or spread in order to plan the most effective therapy. Prostate cancer, for example, is managed by several alternative strategies. One of every 10 men currently develops prostate cancer at some point in his life. In some cases local-regional therapy is utilized, consisting of surgery or radiation, while in other cases systemic therapy is instituted, such as chemotherapy or hormonal therapy. In addition, "watchful waiting" is a treatment option for elderly patients or those in poor health. In addition, "watchful waiting" is a treatment option for men with early stage cancer, or for elderly patients, since untreated prostate cancer may take years to reach a problematic stage.

Current treatment decisions for individual prostate cancer patients are frequently based on the stage of disease at diagnosis and the overall health or age of the patient. It has been reported that DNA ploidy can aid in predicting the course of disease in patients with advanced disease (stage C and D1) (Lee et al., *Journal of Urology* 140:769-774 (1988)). In addition, the pretreatment level of the prostate specific antigen (PSA) has been used to estimate the risk of relapse after surgery and other types of treatment (Pisansky et al., *Cancer* 79:337-344 (1997)). However, a substantial proportion of patients with elevated or rising PSA levels after surgery remain clinically free of symptoms for extended periods of time (Frazier et al., *Journal of Urology* 149:516-518 (1993)). Therefore, even with these additional factors, practitioners are still unable to accurately predict the course of disease for all prostate cancer patients. The inability to differentiate tumors that will progress from those that will remain quiescent has created a dilemma for treatment decisions. There is clearly a need to identify new markers in order to separate patients with good prognosis who may not require further therapy from those more likely to relapse who might benefit from more intensive treatments.

Several side effects of radical prostatectomy (surgical removal of the prostate gland), radiation therapy and hormonal therapy have been documented. The side effects of surgery include discomfort with urination, urinary urgency, impotence, and the morbidity associated with general anesthesia and a major surgical procedure. Common complications associated with external-beam radiation therapy include impotence, discomfort with urination, urinary urgency, and diarrhea. The side effects of anti-androgen hormone therapy can include loss of libido, the development of breast tissue, and osteoporosis. Given the complications associated with some prostate cancer therapies, a marker that could distinguish between tumors that require aggressive treatments and those that require conservative treatment could result in higher survival rates and greater quality of life for prostate cancer patients. Thus, a need exists for a biomarker that can determine prostate cancer patient prognosis. The present invention satisfies this need and provides related advantages as well.

SUMMARY OF THE INVENTION

The invention provide a method of identifying a biomarker that is diagnostic for survival of a patient with a prostate neoplastic condition. The method consists of (a) measuring the level of IAPs in a neoplastic prostate cell-containing sample from patients with a prostate neoplastic condition, and (b) identifying a correlation between the level of IAPs in a sample from a patient with the survival of that patient, where the correlation of an IAP with survival in patients indicates the IAP is a biomarker diagnostic of survival of a patient with a prostate neoplastic condition. Also provided is a method of determining a prognosis for survival for a patient with a prostate neoplastic condition. The method consists of (a) measuring the level of XIAP in a neoplastic prostate cell-containing sample from the patient, and (b) comparing the level of XIAP in the sample to a reference level of XIAP, where an increased level of XIAP in the sample correlates with increased survival of the patient. The invention further provides a method of determining a prognosis for survival for a patient with a prostate neoplastic condition. The method consists of (a) measuring the level of two or more IAPs selected from the group consisting of XIAP, cIAP1, and cIAP2 in a neoplastic prostate cell-containing sample from a patient, and (b) comparing the level of the two or more IAPs in the sample to a reference level of the IAPs, where an increased level of XIAP and decreased level of cIAP1 or cIAP2 in the sample correlates with increased survival of the patient.

BRIEF DESCRIPTION OF THE DRAWINGS

FIG. 4 shows the nucleotide and amino acid sequences for XIAP, cIAP1, and cIAP2.

DETAILED DESCRIPTION OF THE INVENTION

This invention is directed to methods for determining a prognosis for survival for a patient with a prostate neoplastic condition. The methods of the invention are applicable to patients with prostate cancer or other prostate neoplastic conditions and allow rapid and efficient determination of a prognosis for a patient. The methods are based on comparisons of the level of one or more IAP biomarkers in a neoplastic prostate cell-containing sample from patients to a reference level of the biomarker. The biomarker level is used to determine, for example, if a tumor is likely to recur, metastasize, or result in death of the patient.

One advantage of the methods of the invention is that this knowledge can be used by medical practitioners and patients to make an informed choice as to the best course of treatment for that patient. Patients with a biomarker profile that predicts a poor prognosis can choose more aggressive treatment options which can result in higher survival rates. Conversely, patients with a biomarker profile that predicts a good prognosis can choose less aggressive or no treatment options which can result in greater quality of life for patients.

Another advantage of the methods of the invention is that a prognosis can be determined while the patient is still at an early stage of the disease when treatment can be most effective. In addition, the methods of the invention can be used to monitor the effectiveness of a particular treatment during or after treatment. Moreover, the methods of the invention use routine assays that can be performed quickly and efficiently in a standard medical laboratory setting.

The invention is also directed to methods for diagnosing a prostate neoplastic condition in a male subject. The methods of the invention are applicable to subjects who may or may not be at risk for, or be suspected of having, a prostate neoplastic condition. The methods are based on comparison of the level of one or more IAP biomarkers in a neoplastic prostate cell-containing sample from a subject to a reference level of the biomarker. For example, the reference level can be determined from a non-neoplastic prostate cell-containing sample from the same subject or from a group of subjects. An IAP biomarker level that is diagnostic of a prostate neoplastic condition can be used to screen subjects for prostate neoplastic conditions. The IAP biomarker level can be used alone or in combination with other diagnostic markers to diagnose a prostate neoplastic condition in a subject.

One advantage of this method of the invention is that a diagnosis can be determined while the subject is still at an early stage of the disease when treatment can be most effective. In addition, this method uses routine assays that can be performed quickly and efficiently in a standard medical laboratory setting.

Figure 1:
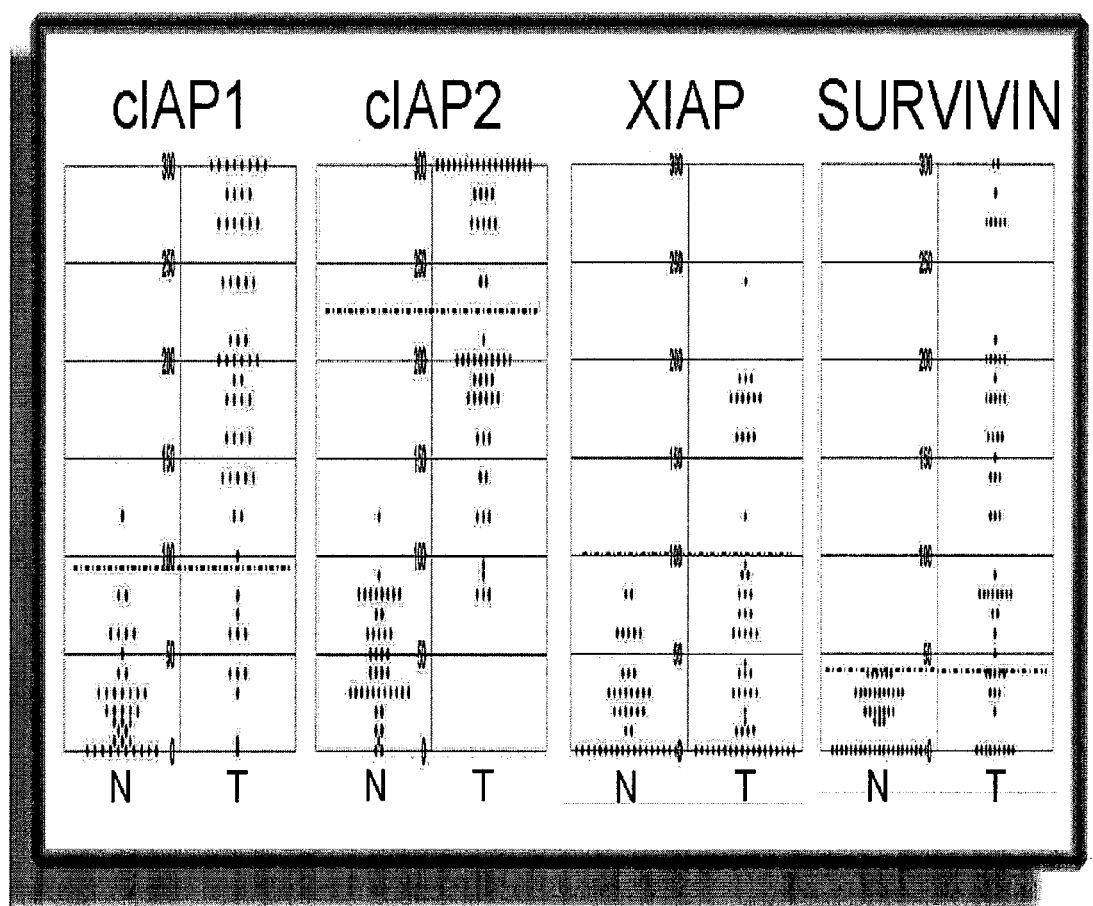
FIG. 1 shows immunoscores for cIAP1, cIAP2, XIAP, and Survivin obtained from normal prostatic epithelium (N) and prostate cancers (T).

In one embodiment, a prognosis for survival for a patient with a prostate neoplastic condition was determined by measuring the level of XIAP in a neoplastic prostate cell-containing sample from the patient and comparing the level of XIAP in the sample to a reference level of XIAP. An increased level of XIAP in the sample correlated positively with increased chance of survival of the patient. Briefly, adenocarcinoma biopsy specimens and case-matched samples containing normal prostatic epithelium were immunostained and evaluated for the level of XIAP, cIAP1, cIAP2, and Survivin polypeptides. To analyze the relationship of these IAP polypeptides to patient survival, comparisons of the immunoscores obtained for normal prostatic epithelium and prostate cancers were used to set logical cut-offs for the dichotomization of data (see FIG. 1). Kaplan-Meier curves and log rank tests demonstrated statistically significant associations of cIAP1, cIAP2, and XIAP with disease-free survival (DFS). While higher levels of cIAP1 and cIAP2 were associated with shorter DFS (p=0.05 and p=0.006 respectively), higher XIAP was correlated with longer DFS (p=0.02) (see Example I). Therefore, the level of XIAP in a neoplastic cell-containing sample from a patient can be used to determine a prognosis for survival for that patient. The methods of the invention also provide for using the level of cIAP1 or cIAP2, or combinations of cIAP1, cIAP2, and XIAP, to determine a prognosis for survival for a patient with a prostate neoplastic condition. In addition, the level of one or more IAP biomarker can be used to diagnose whether a subject has a prostate neoplastic condition.

As used herein, the term "level" refers to the amount, accumulation, or rate of a biomarker molecule. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a molecule accumulated in a cell, including, for example, the amount of particular post-synthetic modifications of a molecule such as a polypeptide, nucleic acid or small molecule. The term can be used to refer to an absolute amount of a molecule in a sample or to a relative amount of the molecule, including amounts determined under steady-state or non-steady-state conditions. The expression level of a molecule can be determined relative to a control component molecule in a sample.

When used in reference to XIAP mRNA or polypeptide expression, the term level refers to the extent, amount, or rate of synthesis of the nucleic acid sequence shown as SEQ ID NO:1 or the XIAP polypeptide shown as SEQ ID NO:2, or substantially the same nucleotide or amino acid sequences. Substantially the same sequence is intended to mean the sequence contains a considerable degree of sequence identity or similarity, such as at least 70%, 80%, 90%, 95%, 98%, or 100% sequence identity or similarity, to a reference nucleotide or amino acid sequence. Conservative and non-conservative changes, gaps, and insertions to a sequence can be compared to a reference sequence using available algorithms and programs such as the Smith-Waterman algorithm and the BLAST homology search program (Altschul et al., *J. Mol. Biol.* 215:403-410 (1990)). When used in reference to cIAP1 mRNA or polypeptide, the term level refers to the extent, amount, or rate of synthesis of the nucleic acid sequence shown as SEQ ID NO:3 or the cIAP1 polypeptide shown as SEQ ID NO:4, or substantially the same nucleotide or amino acid sequences. When used in reference to cIAP2 mRNA or polypeptide, the term level refers to the extent, amount or rate of synthesis of the nucleic acid sequence shown as SEQ ID NO:5 or the cIAP2 polypeptide shown as SEQ ID NO:6, or substantially the same nucleotide or amino acid sequences. A level of these biomarkers of prostate neoplastic conditions can be a gene expression level or a polypeptide expression level.

A gene expression level of a molecule is intended to mean the amount, accumulation, or rate of synthesis of a biomarker gene. The gene expression level can be represented by, for example, the amount or transcription rate of hnRNA or mRNA encoded by a gene. A gene expression level similarly refers to an absolute or relative amount or a synthesis rate determined, for example, under steady-state or non-steady-state conditions.

A polypeptide expression level is intended to mean the amount, accumulation, or rate of synthesis of a biomarker polypeptide. The polypeptide expression level can be represented by, for example, the amount or rate of synthesis of the polypeptide, a precursor form or a post-translationally modified form of the polypeptide. Various biochemical forms of a polypeptide resulting from post-synthetic modifications can be present in a cell contained in a sample. Such modifications include post-translational modifications, proteolysis, and formation of macromolecular complexes. Post-translational modifications of polypeptides include, for example, phosphorylation, lipidation, prenylation, sulfation, hydroxylation, acetylation, addition of carbohydrate, addition of prosthetic groups or cofactors, formation of disulfide bonds and the like. In addition, it is understood that fragments of a polypeptide are included within the definition of a polypeptide expression level. Fragments can include, for example, amino terminal, carboxyl terminal, or internal deletions of a full length polypeptide. Accumulation or synthesis rate with or without such modifications is included within the meaning of the term. Similarly, a polypeptide expression level also refers to an absolute amount or a synthesis rate of the polypeptide determined, for example, under steady-state or non-steady-state conditions.

As used herein, the term "neoplastic prostate cell" refers to any cell that is in, or originated in, the prostate that is transformed such that it proliferates without normal homeostatic growth control. Such cells can result in a benign or malignant prostate lesion of proliferating cells.

As used herein, the term "prostate neoplastic condition" refers to any condition that contains neoplastic prostate cells. Prostate neoplastic conditions include, for example, prostate interepithelial neoplasia (PIN) and prostate cancer. Prostate cancer is an uncontrolled proliferation of prostate cells which can invade and destroy adjacent tissues as well as metastasize. Primary prostate tumors can be sorted into stages using classification systems such as the Gleason score. The Gleason score evaluates the degree of differentiation of the cells in a sample. A lower score (such as 1, 2, 3 or 4) indicates that the cells in the sample are differentiated and fairly normal looking, moderate scores such as 5, 6, or 7 indicate that the cells are moderately differentiated, and higher scores such as 8, 9, or 10 indicate poorly differentiated cells. The stage of overall disease, for example, for prostate cancer can be accessed using staging systems such as the Jewett-Whitmore system or the TNM (tumor, node, metastases) system. The Jewett system classifies prostate cancer into one of four stages distinguished by the letters A, B, C, and D. Subdivisions that reflect specific conditions within each category can also be added to the Jewett system and this expanded alphanumeric system is called the Jewett-Whitmore system. The TNM system uses stages generally similar to those of the Jewett-Whitmore system but with expanded alphanumeric subcategories to describe primary tumors (T), regional lymph node involvement (N) or distant metastasis (M). Similarly, there are classifications known by those skilled in the art for the progressive stages of precancerous lesions or PIN. The methods herein are applicable for the diagnosis of any or all stages of prostate neoplastic conditions.

As used herein, the term "sample" is intended to mean any biological fluid, cell, tissue, organ or portion thereof, that includes or potentially includes a neoplastic prostate cell. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid molecule or polypeptide preparation.

A sample can be prepared by methods known in the art suitable for the particular format of the detection method. For example, in the case of solid tumors which have not metastasized, a tissue sample from the surgically removed tumor can be obtained and prepared for testing by conventional techniques. Alternatively, a body fluid sample, such as a lymph, blood or serum sample, or an exudate fluid sample such as the cancerous organ exudate (e.g., exudate from the prostate) can be collected and used as the sample to be analyzed. In the case of any metastasized cancer, cells can be drawn from a body fluid such as lymphatic fluid, blood, serum, or a distally infected organ or exudate thereof. While IAP levels will typically be measured within the cancerous cells of a patient, levels of IAPs can also be measured in a body fluid sample (e.g., serum) as a result of an IAP having been secreted or otherwise released from cells (e.g., by cell rupture).

As used herein, the term "reference level" refers to a level of expression of an IAP used to evaluate the level of expression of the IAP in a neoplastic prostate cell of a patient. For example, when the level of XIAP, cIAP1 or cIAP2 in the neoplastic cells of a patient are higher than the reference level of XIAP, cIAP1 or cIAP2, the cells will be considered to have a high level of expression, or overproduction, of XIAP, cIAP1 or cIAP2. Conversely, when the level of XIAP, cIAP1 or cIAP2 in the neoplastic cells of a patient are lower than the reference level, the cells will be considered to have a low level of expression, or underproduction, of XIAP, cIAP1 or cIAP2.

As used herein, the terms "high level" or "overproduction" of XIAP, cIAP1 or cIAP2 is related to a level of XIAP, cIAP1 or cIAP2 above a determined reference level value which is likely different for each cancer type. Thus, in accordance with the present invention a reference level of XIAP, cIAP1 or cIAP2 in a particular neoplastic cell type is identified as a cut-off value, above which there is a significant correlation between the presence of XIAP, cIAP1 or cIAP2 and increased or decreased patient survival. Those of skill in the art will recognize that some cut-off values are not absolute in that clinical correlations are still significant over a range of values on either side of the cutoff; however, it is possible to select an optimal cutoff value (e.g. varying H-scores, and the like) of XIAP or cIAP1 for each neoplastic cell type. It is understood that improvements in optimal cutoff values could be determined depending on the sophistication of statistical methods used and on the number and source of samples used to determine reference level values for the different neoplastic cell types.

The reference level can be determined by a plurality of methods, provided that the resulting reference level accurately provides a level of XIAP, cIAP1 or cIAP2 above which exists a first group of patients having a different probability of survival than that of a second group of patients having XIAP, cIAP1 or cIAP2 levels below the reference level. The reference level can be determined by, for example, measuring the level of expression of XIAP, cIAP1 or cIAP2 in non-transformed cells from the same tissue as the tissue of the neoplastic cells to be tested. The reference level can also be a level of XIAP, cIAP1 or cIAP2 of in vitro cultured cells which may or may not have been manipulated to simulate tumor cells, or may have been manipulated in any other manner which yields expression levels which accurately determine the reference level.

The reference level can also be determined by comparison of XIAP, cIAP1 or cIAP2 levels in populations of patients having the same cancer. This can be accomplished, for example, by histogram analysis, in which an entire cohort of patients are graphically presented, wherein a first axis represents the level of XIAP, cIAP1 or cIAP2 and a second axis represents the number of patients in the cohort whose neoplastic cells express XIAP, cIAP1 or cIAP2 at a given level. Two or more separate groups of patients can be determined by identification of subsets populations of the cohort which have the same or similar levels of XIAP, cIAP1 or cIAP2 Determination of the reference level can then be made based on a level which best distinguishes these separate groups.

The reference level can be a single number, equally applicable to every patient, or the reference level can vary, according to specific subpopulations of patients. For example, older men might have a different reference level than younger men for the same cancer. Furthermore, the reference level can be some level determined for each patient individually. For example, the reference level might be a certain ratio of XIAP, cIAP1 or cIAP2 in the neoplastic cells of a patient relative to XIAP, cIAP1 or cIAP2 levels in non-tumor cells within the same patient. Thus the reference level for each patient can be proscribed by a reference ratio of XIAP, cIAP1 or cIAP2, wherein the reference ratio can be determined by any of the methods for determining the reference levels described herein.

As used herein, the term "specifically reactive" when used in reference to an antibody refers to the discriminatory binding of the antibody to the indicated target polypeptide. For such binding to be discriminating, the antibody will not substantially cross react with other polypeptides. Specific reactivity can include binding properties such as binding specificity, binding affinity and binding avidity. For example, an antibody can bind a target polypeptide with a binding affinity (Kd) of about $10^{-4}$ M or more, $10^{-6}$ M or more, $10^{-7}$ M or more, $10^{-8}$ M or more, $10^{-9}$ M or more, or $10^{-10}$ M or more. Several methods for detecting or measuring antibody binding are known in the art and disclosed herein.

As used herein, the term "disease free survival" refers to the lack of detectable disease recurrence and the fate of a patient after diagnosis i.e. a patient who is alive without disease recurrence. For example, if the patient has prostate cancer, disease recurrence would be recurrence of a prostate tumor or metastasis from such as tumor. The phrase "overall survival" refers to the fate of the patient after diagnosis, regardless of whether the patient has a recurrence of the disease.

As used herein, the term "risk of recurrence" refers to the probability of disease recurrence or spread in a patient subsequent to diagnosis of a prostate neoplastic condition, wherein the probability is determined according to the process of the invention.

The invention relates, in part, to the use of IAPs as biomarkers for prognosing survival for a patient with a neoplastic prostate condition. The IAP (inhibitor of apoptosis) polypeptides represent a family of evolutionarily conserved apoptosis suppressors (reviewed by LaCasse et al. Oncogene 17:3247-3259 (1998); Deveraux and Reed Genes and Dev. 13:239-252 (1999)). IAPs contain the BIR (baculovirus iap repeat) domains, which are zinc-binding folds important for their anti-apoptotic activity. Although IAP-family proteins can exhibit several functions, most bind and potently inhibit activated caspases, including the effector caspases 3 and 7, as well as the initiator caspase 9. In addition, some IAPs have been shown to have a role as mediators and regulators of the anti-apoptotic activity of v-Rel and NF-κB transcription factor families. For example, IAPs have been shown to be induced by NF-κB or v-Rel in cell lines and HIAP-1 and HIAP-2 have been shown to activate NF-κB possibly forming a positive feed-back loop.

The baculovirus IAPs, Cp-IAP and Op-IAP, were the first members of this family to be identified based on their ability to functionally complement defects in the cell death inhibitor p35, a baculovirus protein that binds to and inhibits caspase. Subsequently, Subsequently, eight human IAPs have been identified, including X chromosome-linked IAP (XIAP)/hILP, cellular Inhibitor-of-Apoptosis Protein-1 (cIAP-1)/HIAP-2, cIAP2/HIAP-1, Neuronal Apoptotic Inhibitory Protein (NAIP), Apollon (BRUCE), ML-IAP (Livin), ILP-2, and Survivin. Mouse orthologs of most human IAPs have also been identified, indicating conservation of the IAP gene family in mammals.

Defects in apoptosis can contribute to a wide variety of more aggressive tumor phenotypes, including conferring an ability of tumor cells to survive after detachment from extracellular matrix and thus facilitating metastases. Tumor cells with resistance to apoptosis have also recently been shown to survive and grow intravascularly, when adherent to endothelial cells in distal capillary beds. Some IAP-family proteins are over-produced in cancers, suggesting that IAP-mediated suppression of apoptosis can contribute to tumor pathogenesis or progression. For example, Survivin is expressed abundantly in fetal tissues, but scarcely present in most adult tissues. High levels of Survivin protein have been reported in many types of human cancers, suggesting that re-activation of expression of this gene represents a common event in tumorigenesis. Higher levels of Survivin immunostaining have been correlated with shorter survival in one study of patients with Dukes' stage B colon cancer. Unlike other IAPs, Survivin expression is regulated in a cell cycle-dependent manner, with maximum levels occurring during G2/M phase, and the protein localizes to mitotic spindle microtubules and midbodies of dividing cells. Similarly, the ML-IAP (Livin) protein is not expressed at detectable levels in most normal adult tissues, but is present in melanomas and perhaps some other types of cancers. Thus, elevations in the levels of certain IAP-family proteins can occur in tumors, conferring a selective survival advantage.

Apoptosis regulators function in several different biochemical pathways of apoptosis. One of the major pathways for apoptosis induction involves release of cytochrome c from mitochondria. Upon entering the cytosol, cytochrome c binds the caspase-activating protein Apaf1, which forms large oligomers and binds pro-Caspase-9. The oligomeric complex of Apaf1 and Caspase-9 is called the "apoptosome". Apaf1-mediated activation of pro-Caspase-9 then initiates a cascade of proteolytic activation of downstream caspases, with Caspase-3 representing the next protease in this pathway. Loss of Apaf1 expression has been associated with malignant transformation and resistance to chemotherapy in cell culture models, indicating that APAF1 is a tumor suppressor gene.

However, in addition to reducing their Apaf1 expression, a tumor can use other mechanisms for regulating apoptosome assembly or function. For instance, certain IAPs, such as XIAP, cIAP1, cIAP2, Survivin, Livin, and ILP-2 which have been reported to bind and inhibit (directly or indirectly) Caspase-9. Similarly, the anti-apoptotic protein TUCAN also binds pro-Caspase-9, preventing its association with Apaf1. Over-expression of TUCAN has been reported in a study of stage II colon cancer, and found to be present at higher levels in the tumors of patients who relapsed after surgical excision of their primary tumors and who died of disease.

Several mitochondrial proteins contribute to apoptotic process and activation of caspases. For example, mitochondrial intermembrane-associated protein, Smac, binds to IAPs when released from mitochondria and eliminates the inhibitory activity of IAPs, promoting Caspase-9 activation in the apoptosome complex. Bcl-2 and Bcl-XL, the anti-apoptotic members of Bcl-2 family reside mainly in mitochondrial membranes and inhibit apoptosis-associated mitochondrial cytochrome c release. Bcl-2 blocks additionally Smac translocation, thereby impeding Caspase activation and the apoptotic process. Pro-apoptotic members of the Bcl-2 family such as Bax and Bid can translocate from other cellular localizations to mitochondria, an event which is associated with a change in conformation of Bax followed by the release of cytochrome c from mitochondria. There are, however, mitochondrially regulated cell death pathways that are independent of caspase activation. Apoptosis-inducing factor (AIF) has been shown to be released from mitochondria whereupon it translocates to nuclei and stimulates chromatin condensation and stage I DNA fragmentation.

XIAP, cIAP1, and cIAP2 have been shown to bind and directly inhibit caspases 3, 7, and 9, but not caspases 1, 6, 8, or 10 or CED3 (Deveraux et al., supra, 1997, Roy et al., *EMBO J.* 16:6914-6925 (1997)). These IAPs block caspase activation and apoptosis downstream of Bax, Bik, Bak and cytochrome c (Deveraux et al., supra, 1997, Roy et al., supra 1997). XIAP, cIAP1, and cIAP2 have been detected in a variety of tumor cell lines (Tamm et al., *Clinical Cancer Res.* 6:1796-1803 (2000)). However, the role of these IAPs in cancer differs depending on the particular type of cancer. The importance of apoptosis regulators, such as XIAP, cIAP1, and cIAP2, which have roles in regulating transmission of the apoptotic signal and in the maintenance of normal growth control is illustrated herein by the observed correlations of aberrant expression of apoptosis regulators with poor prognosis for patients with a prostate neoplastic condition.

The invention provides a method of identifying a biomarker that is diagnostic for survival of a patient with a prostate neoplastic condition. The method consists of (a) measuring the level of IAPs in a neoplastic prostate cell-containing sample from patients with a prostate neoplastic condition, and (b) identifying a correlation between the level of IAPs in a sample from a patient with the survival of that patient, where the correlation of an IAP with survival in the patients indicates the IAP is a biomarker diagnostic of survival of a patient with a prostate neoplastic condition.

Several pathological conditions that affect the prostate, such as benign prostatic hyperplasia (BPH)/enlarged prostate, prostatic intraepithelial neoplasia (PIN), and prostate carcinoma are prevalent in men over the age of 50. The normal prostate is composed of glands and stroma. The glands are seen in cross section to be rounded to irregularly branching. These glands represent the terminal tubular portions of long tubuloalveolar glands that radiate from the urethra. The glands are lined by two cell layers: an outer low cuboidal layer and an inner layer of tall columnar mucin-secreting epithelium. These cells project inward as papillary projections. The fibromuscular stroma between the glands accounts for about half of the volume of the prostate.

Benign prostatic hyperplasia (BPH) is the nonmalignant, uncontrolled growth of cells in the prostate gland. This cell growth usually occurs in the tissue that surrounds the urethra as it passes through the prostate gland to the bladder. As BPH progresses, the gland constricts the urethra and obstructs urine outflow. As evident in the name, the hyperplastic prostate cells in BPH are not neoplastic.

Prostate neoplastic conditions are characterized by neoplastic prostate cells. For example, PIN and prostate cancer are prostate neoplastic conditions. Prostatic intraepithelial neoplasia (PIN) is dysplasia of the epithelium lining prostate glands, and is a possible precursor of prostatic carcinoma. The appearance of PIN may precede carcinoma by 10 or more years. It can be divided into low grade and high grade PIN. PIN does not routinely increase the serum prostate specific antigen (PSA).

PIN usually involves an acinus or a small cluster of acini, but it can be more extensive on occasion. The acini are usually medium-sized to large, with rounded borders. The partial involvement of an acinus is a helpful feature to distinguish PIN from adenocarcinoma. PIN is characterized histologically by progressive basal cell layer disruption, loss of markers of secretory differentiation, nuclear and nucleolar abnormalities, increasing proliferative potential, increasing microvessel density, variation in DNA content, and allelic loss. Unlike adenocarcinoma, with which it can coexist, glands with PIN retain an intact or fragmented basal cell layer.

Low grade PIN has epithelial cells that are crowded and irregularly spaced, with nuclei that are hyperchromatic and pleomorphic, with small nucleoli. High grade PIN has even more hyperchromatism and pleomorphism, the cells are more crowded and heaped up, and nucleoli can be prominent. Immunohistochemical staining with antibody to low molecular weight keratin can help to identify the fragmented basal cell layer. Anti-androgenic drug therapy may cause regression of PIN.

The appearance of PIN warrants increased surveillance of the prostate for development of an invasive carcinoma because the presence of high grade PIN is correlated an increased risk for subsequent appearance of adenocarcinoma.

Prostate cancers are generally slow-growing malignancies that are characterized by an imbalance in the rates of cell division and cell death. Tissue kinetics studies indicate that insufficient programmed cell death represents one explanation for the gradual accumulation of prostate cancer cells in vivo in humans. The progression of localized hormone-dependent prostate cancers to metastatic, hormone-refractory disease is also associated with dysregulation of normal apoptotic mechanisms.

Adenocarcinoma of the prostate is the most common non-skin malignancy in elderly men. It is rare before the age of 50, but autopsy studies have found prostatic adenocarcinoma in over half of men more than 80 years old. Many of these carcinomas are small and clinically insignificant. However, some are not, and prostatic adenocarcinoma is second only to lung carcinoma as a cause for tumor-related deaths among males. Men with a higher likelihood of developing a prostate cancer (in the U.S.) include those of older age, black race, and family history. Those with an affected first-degree relative have double the risk. Other risk factors include smoking and a high fat diet.

Prostate cancers can be detected by digital examination, by ultrasonography (transrectal ultrasound), or by screening with a blood test for prostate specific antigen (PSA). None of these methods can reliably detect all prostate cancers, particularly the small cancers. PSA is a glycoprotein produced almost exclusively in the epithelium of the prostate gland. The PSA is normally less than 4 ng/mL (normal ranges vary depending upon which assay is used). A mildly increased PSA (4 to 10 ng/mL) in a patient with a very large prostate can be due to nodular hyperplasia, or to prostatitis, rather than carcinoma. A rising PSA (more than 0.75 ng/mL per year) is suspicious for prostatic carcinoma, even if the PSA is in the normal range. Transrectal needle biopsy, often guided by ultrasound, is useful to confirm the diagnosis, although incidental carcinomas can be found in transurethral resections for nodular hyperplasia.

Prostatic adenocarcinomas are composed of small glands that are back-to-back, with little or no intervening stroma. Cytologic features of adenocarcinoma include enlarged round, hyperchromatic nuclei that have a single prominent nucleolus. Less differentiated carcinomas have fused glands called cribriform glands, as well as solid nests or sheets of tumor cells, and many tumors have two or more of these patterns. Prostatic adenocarcinomas often arise in the posterior outer zone of the prostate and are often multifocal. Several grading systems based on pathological criteria are known in the art and described herein for identifying and staging prostate tumors. For a review of markers in normal versus pathological tissues, see, for example, *Campbell's Urology*, Seventh Edition, W.B. Saunders Company, Philadelphia (1998).

As stated further above, the invention provides a method of identifying a biomarker that is prognostic for survival of a patient with a prostate neoplastic condition by (a) measuring the level of IAPs in a neoplastic prostate cell-containing sample from patients with a prostate neoplastic condition, and (b) identifying a correlation between the level of IAPs in a sample from a patient with the survival of that patient, where the correlation of an IAP with survival in the patients indicates the IAP is a biomarker diagnostic of survival of a patient with a prostate neoplastic condition.

This method of the invention is a procedure for screening potential IAP biomarkers in order to find one or more IAP biomarker that is diagnostic for survival of a patient with a prostate neoplastic condition. IAPs that can be measured include-any IAP from any species. For example, the level of human XIAP, cIAP1, cIAP2, and Survivin can be measured in a sample.

The level of an IAP nucleic acid or polypeptide can be measured in a neoplastic prostate cell-containing sample from patients. For example, an antibody specifically reactive with an IAP polypeptide can be used in an immunoblot assay to measure the level of an IAP polypeptide. Methods for measuring the level of a nucleic acid or polypeptide are well known in the art and will be described further below in reference to specific IAP biomarkers. Several types of samples from patients with a prostate neoplastic condition can be assayed as described further above. For example, a sample can be prostate tissue or a fluid such as blood, serum, urine, or semen.

Once a level of an IAP is determined, this value can be correlated with clinical data on the patient from whom the sample was derived. Clinical data on the patient can include, for example, the stage of the initial tumor, whether the tumor metastasized, the treatment option used, and whether the tumor recurred. Clinical data can also include, for example, data on whether the patient is alive or dead. For patients who are alive, they can be categorized as surviving without disease (disease-free survival) or surviving with disease.

The level of IAPs in a sample from a patient can be correlated with the overall survival of that patient or with disease-free survival of the patient. The correlation of an IAP with survival in the patients indicates the IAP is a biomarker diagnostic of survival of a patient with a prostate neoplastic condition. This biomarker can be used, for example, to determine if the patient is at risk for relapse or to determine the proper course of treatment for the patient. In addition, the level of these biomarkers can be used in combination with the levels of other markers such as the level of apoptotic polypeptides or other diagnostic markers.

The invention also provides a method for determining a prognosis for survival for a patient with a prostate neoplastic condition. The method consists of (a) measuring the level of XIAP in a neoplastic prostate cell-containing sample from a patient, and (b) comparing the level of XIAP in the sample to a reference level of XIAP, where an increased level of XIAP in the sample correlates with increased survival of the patient. This method can be used to determine a prognosis for overall survival or disease-free survival. In addition, the level of XIAP can be used in combination with the levels of other markers such as the level of apoptotic polypeptides or other diagnostic markers.

The nucleotide (SEQ ID NO:1) and amino acid (SEQ ID NO:2) sequence of human XIAP are shown in FIG. 4. XIAP has been detected in several tumor cell lines, however its role in predicting patient prognosis is unclear (Tamm et al., supra, 2000). Since XIAP is a suppressor of apoptosis, one might expect that increased levels of XIAP in a neoplastic cell sample would correlate with a lack of apoptosis in these cells and poor patient prognosis. This is the case with acute myelogenous leukemia (AML) patients where patients with increased XIAP levels had significantly shorter survival rates (Tamm et al., supra, 2000). However, in contrast, as disclosed for the first time herein, increased levels of XIAP in prostate cancer samples correlates with increased survival of the patient (see Example I). In addition, increased XIAP levels in patients with non-small cell lung cancer correlated with longer overall survival (Ferreira et al., *Clin. Cancer Res.* 7:2468-2474 (2001)). However, XIAP expression in tumor tissue sections from patients with cervical squamous carcinomas did not correlate with patient survival although other markers did correlate with survival (Liu et al., *Eur. J. Cancer* 37:1104-1110 (2001)). Therefore, increased levels of XIAP did not correlate with patient survival in cervical cancer patients, correlated positively with patient survival in prostate and non-small cell lung cancer patients, and correlated negatively with patient survival in AML patients.

The level of XIAP can be measured in a neoplastic prostate cell-containing sample from a patient. For example, the sample can be a section of prostate tissue that is attached to a microarray. In addition, for example, the sample can be a fluid such as blood, serum, urine, or semen.

In one embodiment, a level of a biomarker, such as XIAP, cIAP1, or cIAP2, can be determined by measuring the amount of a biomarker polypeptide using a binding agent selective for the biomarker, such as an antibody specifically reactive with a biomarker polypeptide.

Essentially all modes of affinity binding assays are applicable for use in determining a level of a biomarker polypeptide, such as XIAP, cIAP1, or cIAP2, in a sample. Such methods are rapid, efficient and sensitive. Moreover, affinity binding methods are simple and can be modified to be performed under a variety of clinical settings and conditions to suit a variety of particular needs. Affinity binding assays that are known and can be used in the methods of the invention include both soluble and solid phase formats. A specific example of a soluble phase affinity binding assay is immunoprecipitation using a biomarker selective antibody or other binding agent. Solid phase formats are advantageous for the methods of the invention since they are rapid and can be performed more easily on multiple different samples simultaneously without losing sensitivity or accuracy. Moreover, solid phase affinity binding assays are further amenable to high throughput screening and automation.

Specific examples of solid phase affinity binding assays include immunohistochemical binding assays, immunoaffinity binding assays such as an ELISA and radioimmune assay (RIA). Other solid phase affinity binding assays are known to those skilled in the art and are applicable to the methods of the invention. Although affinity binding assays are generally formatted for use with an antibody binding molecules that is selective for the analyte or ligand of interest, essentially any binding agent can be alternatively substituted for the selectively binding antibody. Such binding agents include, for example, macromolecules such as polypeptides, peptides, nucleic acid molecules, lipids and sugars as well as small molecule compounds. Methods are known in the art for identifying such molecules which bind selectively to a particular analyte or ligand and include, for example, surface display libraries and combinatorial libraries. Thus, for a molecule other than an antibody to be used in an affinity binding assay, all that is necessary is for the binding agent to exhibit selective binding activity for a biomarker.

The various modes of affinity binding assays, such as immunoaffinity binding assays, include, for example, immunohistochemistry methods, immunoblot methods, solid phase ELISA and RIA as well as modifications thereof. Such modifications thereof include, for example, capture assays and sandwich assays as well as the use of either mode in combination with a competition assay format. The choice of which mode or format of immunoaffinity binding assay to use will depend on the intent of the user. Such methods can be found described in common laboratory manuals such as Harlow and Lane, *Using Antibodies: A Laboratory Manual*, Cold Spring Harbor Laboratory Press, New York (1999).

An antibody useful in the methods of the invention includes a polyclonal and monoclonal antibody, as well as an antigen binding fragment of such antibodies. Methods of preparing polyclonal or monoclonal antibodies are well known to those skilled in the art and are described in Example I and in Harlow and Lane, *Antibodies: A Laboratory Manual*, Cold Spring Harbor Laboratory Press (1988).

An antibody useful in the methods of the invention also includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (*Science* 246:1275-1281 (1989)). These and other methods of making, for example, chimeric, humanized, CDR-grafted, single chain, and bifunctional antibodies are well known to those skilled in the art (Winter and Harris, *Immunol. Today* 14:243-246 (1993); Ward et al., *Nature* 341:544-546 (1989); Harlow and Lane, supra, 1988); Hilyard et al., *Protein Engineering: A practical approach* (IRL Press 1992); Borrabeck, *Antibody Engineering*, 2d ed. (Oxford University Press 1995)).

Formats employing affinity binding can be used in conjunction with a variety of detection labels and systems known in the art to quantitate amounts of biomarkers in the analyzed sample. Detection systems include the detection of bound biomarker by both direct and indirect means. Direct detection methods include labeling of the biomarker-specifically reactive antibody or binding agent. Indirect detection systems include, for example, the use of labeled secondary antibodies and binding agents.

Secondary antibodies, labels and detection systems are well known in the art and can be obtained commercially or by techniques well known in the art. The detectable labels and systems employed with the biomarker-selective binding agent should not impair binding of the agent to the biomarker. Moreover, multiple antibody and label systems can be employed for detecting the bound biomarker-specifically reactive antibody to enhance the sensitivity of the binding assay if desired.

Detectable labels can be essentially any label that can be quantitated or measured by analytical methods. Such labels include, for example, enzymes, radioisotopes, fluorochromes as well as chemi- and bioluminescent compounds. Specific examples of enzyme labels include horseradish peroxidase (HRP), alkaline phosphatase (AP), β-galactosidase, urease and luciferase.

A horseradish-peroxidase detection system can be used, for example, with the chromogenic substrate tetramethylbenzidine (TMB), which yields a soluble product in the presence of hydrogen peroxide that is detectable by measuring absorbance at 450 nm. An alkaline phosphatase detection system can be used with the chromogenic substrate p-nitrophenyl phosphate, for example, which yields a soluble product readily detectable by measuring absorbance at 405 nm. Similarly, a β-galactosidase detection system can be used with the chromogenic substrate o-nitrophenyl-β-D-galactopyranoside (ONPG), which yields a soluble product detectable by measuring absorbance at 410 nm, or a urease detection system can be used with a substrate such as urea-bromocresol purple (Sigma Immunochemicals, St. Louis, Mo.). Luciferin is the substrate compound for luciferase which emits light following ATP-dependent oxidation.

Fluorochrome detection labels are rendered detectable through the emission of light of ultraviolet or visible wavelength after excitation by light or another energy source. DAPI, fluorescein, Hoechst 33258, R-phycocyanin, B-phycoerythrin, R-phycoerythrin, rhodamine, Texas red and lissamine are specific examples of fluorochrome detection labels that can be utilized in the affinity binding formats of the invention. A particularly useful fluorochrome is fluorescein or rhodamine.

Chemiluminescent as well as bioluminescent detection labels are convenient for sensitive, non-radioactive detection of a biomarker and can be obtained commercially from various sources such as Amersham Lifesciences, Inc. (Arlington Heights, Ill.).

Alternatively, radioisotopes can be used as detectable labels in the methods of the invention. Iodine-125 is a specific example of a radioisotope useful as a detectable label.

Signals from detectable labels can be analyzed, for example, using a spectrophotometer to detect color from a chromogenic substrate; a fluorometer to detect fluorescence in the presence of light of a certain wavelength; or a radiation counter to detect radiation, such as a gamma counter for detection of iodine-125. For detection of an enzyme-linked secondary antibody, for example, a quantitative analysis of the amount of bound agent can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

The prognostic formats of the present invention can be forward, reverse or simultaneous as described in U.S. Pat. No. 4,376,110 and U.S. Pat. No. 4,778,751. Separation steps for the various assay formats described herein, including the removal of unbound secondary antibody, can be performed by methods known in the art (Harlow and Lane, supra). For example, washing with a suitable buffer can be followed by filtration, aspiration, vacuum or magnetic separation as well as by centrifugation.

A binding agent selective for a biomarker also can be utilized in imaging methods that are targeted at biomarker-expressing neoplastic cells. These imaging techniques will have utility in identification of residual neoplastic cells at the primary site following standard treatments including, for example, radical prostatectomy, radiation or hormone therapy. In addition, imaging techniques that detect neoplastic prostate cells have utility in detecting secondary sites of metastasis. The biomarker specific binding agent can be radiolabeled with, for example, $^{111}$indium and infused intravenously as described by Kahn et al., *Journal of Urology* 152:1952-1955 (1994). The binding agent selective for a biomarker can be, for example, a monoclonal antibody specifically reactive with a biomarker, such as XIAP, cIAP1, or cIAP2. Imaging can be accomplished by, for example, radioimmunoscintigraphy as described by Kahn et al., supra.

The level of a biomarker, such as XIAP, cIAP1, or cIAP2, also can be determined by measuring the amount of a biomarker mRNA or DNA using a binding agent selective for the biomarker, such as a nucleic acid probe. The level of a biomarker in a sample, for example, the level of XIAP, cIAP1, or cIAP2 can be indicated by measuring the level of nucleic acid encoding the biomarker. Nucleic acids, for example, DNA and RNA, can be detected using amplification procedures such as PCR or RT-PCR or hybridization procedures such as Southern or Northern blots or RNase protection assays. These methods are known to those skilled in the art and are described, for example, in the Current Protocols in Molecular Biology (John Wiley & Sons, 1999); in U.S. Pat. No. 5,882, 864; and the like.

Hybridization methods are applicable for measuring the amount of biomarker RNA as an indicator of biomarker expression levels. There are numerous methods well known in the art for detecting nucleic acid molecules by specific or selective hybridization with a complementary probe. Such methods include both solution hybridization procedures and solid-phase hybridization procedures where the probe or sample is immobilized to a solid support. Descriptions for such methods can be found in, for example, Sambrook et al., supra, and in Ausubel et al., supra. Specific examples of such methods include PCR and other amplification methods such as RT-PCR, 5' or 3' RACE, RNase protection, RNA blot, dot blot or other membrane-based technologies, dip stick, pin, ELISA or two-dimensional arrays immobilized onto chips as a solid support. These methods can be performed using either qualitative or quantitative measurements, all of which are well known to those skilled in the art.

PCR or RT-PCR can be used with isolated RNA or crude cell lysate preparations. PCR is advantageous when there is limiting amounts of starting material. A further description of PCR methods can be found in, for example, Dieffenbach, C. W., and Dveksler, G. S., *PCR Primer: A Laboratory Manual*, Cold Spring Harbor Press, Plainview, N.Y. (1995). Multi-sample formats such as microarrays offer the advantage of analyzing numerous, different samples in a single assay. A particular example of a microarray used in a hybridization format is described further below in the Examples. In contrast, solid-phase dip stick-based methods offer the advantage of being able to rapidly analyze a patient's fluid sample for an immediate result.

Nucleic acid probes useful for measuring the expression level of a biomarker, such as XIAP, cIAP1, or cIAP2, by hybridization include, for example, probes prepared using the nucleotide sequences provided herein (FIG. 4). Nucleic acid molecules corresponding to the entire cDNA sequences and fragments thereof, including oligonucleotides corresponding to XIAP, cIAP1, or cIAP2 nucleotide sequences and which are capable of specifically or selectively hybridizing to XIAP, cIAP1, or cIAP2 RNA, are useful for hybridization methods.

Briefly, for detection by hybridization, nucleic acid probes having detectable labels are added to a neoplastic prostate cell-containing sample or a fluid sample obtained from the individual having, or suspected of having a prostate neoplastic condition under conditions which allow annealing of the probe to biomarker RNA. Conditions are well known in the art for both solution and solid phase hybridization procedures. Moreover, optimization of hybridization conditions can be performed, if desired, by hybridization of an aliquot of the sample at different temperatures, durations and in different buffer conditions. Such procedures are routine and well known to those skilled in the art. Following annealing, the sample is washed and the signal is measured and compared with a suitable control or standard value. The magnitude of the hybridization signal is directly proportional to the expression levels of a biomarker, such as XIAP, cIAP1, or cIAP2.

Nucleic acid probes useful for measuring the expression level of a biomarker, such as XIAP, cIAP1, or cIAP2 by hybridization include, for example, probes prepared using the nucleotide sequences provided herein (FIG. 4). Nucleic acid molecules corresponding to the entire cDNA sequences and fragments thereof, including oligonucleotides corresponding to XIAP, cIAP1, or cIAP2 nucleotide sequences and which are capable of specifically or selectively hybridizing to XIAP, cIAP1, or cIAP2 RNA, are useful for hybridization methods.

A reference level is a level a biomarker, such as XIAP, cIAP1, or cIAP2-2, used to evaluate the level of the biomarker in neoplastic cells of a patient. Specifically, when the level of a biomarker in the neoplastic cells of a patient are higher than the reference level, the cells will be considered to have a high level of, or overproduction, of the biomarker. Conversely, when the level of biomarker in the neoplastic cells of a patient are lower than the reference level, the cells will be considered to have a low level of, or underproduction, of the biomarker.

A high level of a biomarker, such as XIAP, cIAP1, or cIAP2, or overproduction of a biomarker gene is related to a level of the biomarker above a determined basal level. Thus, a reference or basal level of a biomarker, such as XIAP, cIAP1, or cIAP2, in a neoplastic prostate cell is identified as a "cutoff" value, above which there is a significant correlation between the presence of the biomarker and increased or decreased disease recurrence or spread. Those of skill in the art will recognize that some "cutoff" values are not sharp in that clinical correlations are still significant over a range of values on either side of the cutoff; however, it is possible to select an optimal cutoff value (for example varying H-scores, and the like) of a level of a biomarker for a prostate cancer cell type. It is understood that improvements in optimal cutoff values could be determined, depending on the sophistication of statistical methods used and on the number and source of samples used to determine reference or basal values.

Such overproduction is not typically calculated in terms of absolute biomarker levels, but is determined using relative measurements. These relative measurements are illustrated for quantitation purposes with an internal standard; however, it will be appreciated that other standards or methods of determination can be used, such as comparison with external standards, biomarker polypeptide measurements, biomarker mRNA measurements, absolute values of protein, mRNA or DNA levels, and the like.

A reference level can also be determined by comparison of biomarker levels in populations of patients having a prostate neoplastic condition, such as patients having prostate cancer of the same stage. This can be accomplished by histogram analysis, in which the entire cohort of patients tested are graphically presented, wherein a first axis represents the level of a biomarker, and a second axis represents the number of patients in the cohort whose neoplastic cells contain the biomarker at a given level. Two or more separate groups of patients can be determined by identification of subsets populations of the cohort which have the same or similar levels of the biomarker. Determination of the reference level can then be made based on a biomarker level that best distinguishes these separate groups.

Verification that the reference level distinguishes the likelihood of disease recurrence or spread in patients with prostate neoplastic conditions expressing below-reference biomarker levels versus cancer patients expressing above-reference biomarker levels can be carried out using single variable or multi-variable analysis. These methods determine the likelihood of a correlation between one or more variables and a given outcome. In the specific case, the methods will determine the likelihood of a correlation between a biomarker levels (or biomarker level coupled with another variable) and disease-free or overall survival of patients with a prostate neoplastic condition. Any one of a plurality of methods well known to those of ordinary skill in the art for carrying out these analyses can be used. Examples of single variable analysis is the Kaplan-Meir method or the log-rank test. An example of multi-variable analysis is the Cox proportional-hazards regression model (see, for example, Example I).

Population-based determination of reference levels, for example, by histogram analysis can be carried out using a cohort of patients sufficient in size in order to determine two or more separate groups of patients having different biomarker levels. Typically, such a cohort comprises at least 25 patients, such as at least 50 patients, including at least 75 patients, and at least 100 patients. Similarly, verification of determined reference levels can also comprise at least 25 patients, such as at least 50 patients, including at least 75 patients, and at least 100 patients.

The reference level can be a single number, equally applicable to every patient, or the reference level can vary according to specific subpopulations of patients. For example, younger men might have a different reference level than older men for the same cancer. Furthermore, the reference level can be a level determined for each patient individually. For example, the reference level might be a certain ratio of a biomarker level in the neoplastic cells of a patient relative to the biomarker level in non-neoplastic cells within the same patient. Thus the reference level for each patient can be proscribed by a reference ratio of biomarker levels, wherein the reference ratio can be determined by any of the methods for determining the reference levels described above.

Further, while a reference level can separate two groups of patients, it is within the scope of the invention that numerous reference values might exist which separate a plurality of populations. For example, two reference values can separate a first group of patients with high levels of a biomarker from a second group of patients with intermediate levels the biomarker, and from a third group of patients with low levels of the biomarker. The number of different reference levels can be sufficient to proscribe a curve, such as a continuous line, which describes the likelihood of disease-free or overall survival in a patient as a function of the biomarker level in that patient. Such a curve will constitute a "continuous" biomarker level, where the likelihood of disease free or overall survival in a patient is proportional to the biomarker level in that patient. Two or more biomarker levels also can be represented by such a curve.

The reference level can also represent the level of a biomarker polypeptide, such as XIAP, cIAP1, or cIAP2, in one or more compartments of the cell. Typically, the reference level will represent the level of biomarker protein in (a) the whole cell, (b) the nucleus, or (c) the cytosol. This level will be useful when cell compartmentalization of the polypeptide correlates with the risk of disease recurrence or spread. Similarly, the reference level can be a ratio of levels of biomarker protein in the different compartments (for example, the ratio of nuclear biomarker protein to whole cell biomarker protein, or the ratio of nuclear to cytosolic biomarker protein).

The reference level of a biomarker, such as XIAP, cIAP1, or cIAP2, can further be used in conjunction with another variable found to be a statistically significant indicator of the likelihood of disease-free or overall survival for a prostate neoplastic condition. Such indicators include the presence or levels of known prostate neoplastic condition markers (for example, PSA level), or can be clinical or pathological indicators (for example, age, tumor size, tumor histology, clinical stage, family history and the like). For example, clinical stage of a cancer is also a statistically significant indicator of disease-free or overall survival, wherein the reference level of a biomarker can vary according to the clinical stage of the cancer. For example, the level of a biomarker, such as a high levels of XIAP, in conjunction with clinical stage II of a cancer for a given patient, together are indicators for increased likelihood of disease free or overall survival. Hence, the reference level of a biomarker can vary as a function of another statistically significant indicator of disease-free or overall survival for a prostate neoplastic condition.

The levels of biomarkers, such as XIAP, cIAP1, or cIAP2, in a neoplastic prostate cell can correlate with each other and with other molecules because these molecules participate in common dysregulated molecular pathways that contribute to the hyperproliferative state of a neoplastic prostate cell. Therefore two or more biomarkers can be used in the methods of the invention for determining a prognosis for survival for a patient with a prostate neoplastic condition. A second or additional biomarker can be, for example, XIAP, cIAP1, or cIAP2. Furthermore, the use of two or more biomarkers can provide increased prognostic significance or confidence in a prognostic determination.

The level of a biomarker in a sample, for example, the level of XIAP, cIAP1, or cIAP2, can be measured in a sample from a patient at any stage of disease. For example, a sample can be obtained from a patient with early stage prostate cancer, for example, stage B.

Two systems commonly are used for staging prostate cancer: the Jewett-Whitmore system and the TNM (tumor, node, metastases) system. The Jewett system classifies prostate cancer into one of four stages, distinguished by the letters A-D. Stage A indicates a very early stage without symptoms. Cancer typically is discovered accidentally, such as when a patient has surgery for benign prostatic hyperplasia (BPH). Cancer cells are confined to the prostate. Stage B indicates disease that is confined to the prostate, but palpable (detectable by digital rectal exam) or detectable by elevated PSA. Stage C indicates cancer cells have spread outside the prostate capsule (membrane covering the prostate). The spread is localized (confined to the surrounding tissues or seminal vesicles). Stage D indicates that cancer cells have metastasized to lymph nodes, or to distant bones, organs or other tissues.

Subdivisions that reflect specific conditions within each category have been added to the Jewett system. This expanded, alphanumeric system is called the Jewett-Whitmore system. Stages using the Jewett-Whitmore system are described in Table 1.

TABLE 1

| | |
|---|---|
| A1 | (Clinically undetectable) Cancer cells are well differentiated. |
| A2 | Moderately or poorly differentiated. Cancer cells are present in several locations within the prostate. |
| B0 | Confined to the prostate, nonpalpable; PSA elevated. |
| B1 | Single cancerous nodule in one lobe of the prostate. |
| B2 | More extensive, involving one or both prostate lobes. |
| C1 | Localized, extending outside the prostate capsule. |
| C2 | Tumor causes bladder or urethral obstruction. |
| D0 | Metastatic, clinically localized, but showing elevated blood PAP levels. |
| D1 | Regional lymph nodes involved. |
| D2 | Distant lymph nodes, bones or organs involved. |
| D3 | Metastatic patients who relapse after therapy. |

The TNM (Tumor, Node, Metastases) staging system, adopted by the American Joint Committee on Cancer and the International Union Against Cancer in 1992, uses stages generally similar to those of the Jewett-Whitmore System, but with expanded alphanumeric subcategories to reflect specific areas. Stages using the TNM system are described in Table 2.

TABLE 2

| Primary tumor (T) | |
|---|---|
| TX | Tumor cannot be assessed. |
| T0 | No evidence of primary tumor. |
| T1 | Clinically not palpable or visible by imaging, but: |
| T1a | Found incidental to other surgery, present in 5% or less of tissue. |
| T1b | Found incidental to other surgery, present in 5% or more of tissue. |
| T1c | Identified by needle biopsy (performed owing to elevated PSA). |
| T2 | Tumor confined within prostate, involving: |
| T2a | Half a lobe or less of prostate. |
| T2b | Half a lobe, but not both lobes. |
| T2c | Both lobes. |
| T3 | Tumor extending through prostate capsule. |
| T3a | Extension through one lobe. |
| T3b | Extension through both lobes. |
| T3c | Extension into seminal vesicles. |
| T4 | Tumor fixed, invading structures other than seminal vesicles. |
| T4a | Invasion of bladder neck, external sphincter or rectum. |
| T4b | Invasion of muscles and/or pelvic wall. |
| Regional Lymph Nodes (N) | |
| NX | Nodes cannot be assessed. |
| N0 | No regional node metastasis. |
| N1 | Single node metastasis, 2 centimeters (cm) or less at largest point. |
| N2 | Single node metastasis, 2 cm to 5 cm at largest point, or multiple nodes, no larger than 5 cm at largest point. |
| N3 | Metastasis larger than 5 cm in any node. |
| Distant Metastasis (M) | |
| MX | Presence of metastasis cannot be assessed. |
| M0 | No distant metastasis. |
| M1 | Distant metastasis. |
| M1a | Non-regional lymph node(s) involved. |
| M1b | Bone(s) involved. |
| M1c | Other site(s) involved. |

The predictive value of the methods of the invention will be particularly effective in the case of patients in the early stages of disease. This is because the method of the invention can be advantageously effective in determining the risk of metastasis in patients who demonstrate no measurable metastasis at the time of examination. One of ordinary skill in the art would appreciate that the prognostic indicators of survival for cancer patients suffering from stage A cancer may be different from those for cancer patients suffering from stage D cancer.

The methods of the invention can also be used for monitoring the effectiveness of a course of treatment for a patient suffering from a prostate neoplastic condition. The methods consists of determining the level of an IAP in a neoplastic prostate cell sample from the patient prior to the treatment; and determining the level of the IAP in a neoplastic prostate cell sample from the patient after treatment has begun, where comparison of the IAP level prior to treatment with the IAP level after treatment has begun indicates the effectiveness of the treatment. The IAP measuring can be, for example, XIAP, cIAP1, cIAP2, or any combination of these or other biomarkers. These measurements can be taken at different times during the course of treatment or after treatment has been completed. The level of these markers can be used to monitor the effectiveness of treatment either alone or in combination with other markers such as, for example, PSA levels or levels of nucleic acids or polypeptides known to be involved in apoptosis.

As used in the context of a course of treatment, "effectiveness" refers to the ability of the course of treatment to decrease the risk of disease recurrence or spread and therefore to increase the likelihood of disease-free or overall survival of the patient. This method will have particular utility when the level a biomarker, such as XIAP, cIAP1, or cIAP2 in the neoplastic cells of a patient is abnormal compared to the level of cIAP, TUCAN, Apaf1 and Smac in the non-neoplastic cells of the patient. Comparison of biomarker levels in a neoplastic prostate cell-containing sample from a patient before and after treatment will thereby serve to indicate whether a biomarker level is returning to that of non-neoplastic cells, implying a more effective course of treatment, or whether a biomarker level is remaining abnormal or increasing in abnormality, implying a less effective course of treatment. For example, an increase in the level of XIAP in a patient sample after treatment can indicate that treatment is effective because increased levels of XIAP correlate with a lower incidence of prostate neoplastic condition recurrence. Further, a decrease in the level of cIAP1 or cIAP2 in a patient sample after treatment can indicate that treatment is effective because decreased levels of cIAP1 or cIAP2 correlate with a lower incidence of prostate neoplastic condition recurrence.

Several treatment options are available for patients with prostate neoplastic conditions. These include "watchful waiting," surgery, radiation therapy, and hormone therapy. There are risks and possible side effects associated with different treatments. The use of the methods of the invention to predict based on an IAP level within a sample whether a patient has a greater or lesser chance of survival, can aid at determining the proper course of treatment for that particular patient.

The most conservative treatment option is "watchful waiting." Some men may decide not to have treatment immediately if the cancer is growing slowly and not causing symptoms. Instead, they have regular checkups so they can be closely monitored by their doctor. Men who are older or have another serious illness may choose this option. In addition, patients that choose this option may include alternative therapies which include nutrition, medicinal herbs and other naturopathic treatments. A risk associated with watchful waiting is that a patient can have a prostate neoplastic disease that grows rapidly or suddenly between checkups.

Surgery usually removes the entire prostate and surrounding tissues (called a radical prostatectomy). Impotence and incontinence are a possible side effects of surgery. Another kind of surgery is a transurethral resection, which cuts cancer from the prostate but does not take out the entire prostate. This operation is sometimes done to relieve symptoms caused by the tumor before other treatment or in men who cannot have a radical prostatectomy.

Radiation therapy uses high energy rays to kill cancer cells and shrink tumors. It is often used when cancer cells are found in more than one area. Impotence can occur in men treated with radiation therapy. Two types of radiation therapy are used to treat prostate cancer: brachytherapy and external radiation therapy (XRT). Brachytherapy delivers a higher and more focused dose of radiation with fewer side effects and at lower cost than external beam therapy. Brachytherapy is the implantation of tiny, radioactive implants into a cancerous prostate gland. Radiation emitted by the implants kills the malignant tumor.

Hormone therapy involves the use of antiandrogens (an androgen is a male hormone needed for the production of testosterone) to block production of the testosterone cancer cells use to grow. It can be used for prostate cancer that has spread to distant parts of the body. However, not all prostate cancers are sensitive to hormone therapy. Drugs that are used for hormone therapy include: leuprolid acetate (Lupron Depot®), goserelin acetate implant (Zoladex®), bicalutamide (Casodex®), and flutamide (Eulexin®). Growth of breast tissue is a common side effect of hormone therapy.

The invention also provides a method of determining a prognosis for survival for a patient with a prostate neoplastic condition by (a) measuring the level of cIAP2 in a neoplastic prostate cell-containing sample from the patient, and (b) comparing the level of cIAP2 in the sample to a reference level of cIAP2, where an increased level of cIAP2 in the sample correlates with decreased survival of the patient. The invention further provides a method of determining a prognosis for survival for a patient with a prostate neoplastic condition by (a) measuring the level of cIAP1 in a neoplastic prostate cell-containing sample from the patient, and (b) comparing the level of cIAP1 in the sample to a reference level of cIAP1, where an increased level of cIAP1 in the sample correlates with decreased survival of the patient.

Similar to the method described further above for using the level of XIAP to determine a prognosis for survival for a patient with a prostate neoplastic condition, the level of cIAP1 and cIAP2 can be used to determine a prognosis for survival in these patients. However, for both cIAP1 and cIAP2, an increased level of these biomarkers correlates with decreased survival of the patients. As disclosed herein (see Example I), increased or higher levels of cIAP1 and cIAP2 are associated with shorter DFS ($p=0.05$ and $p=0.006$, respectively).

As with the method described further above for using the level of XIAP to determine a prognosis for survival for a patient with a prostate neoplastic condition, the method can be used to determine overall survival or disease-free survival. The sample used for measurement can be, for example prostate tissue or a fluid such as blood, serum, urine, or semen. Measurement of the level of cIAP1 or cIAP2 can be performed, for example, using an antibody specifically reactive with these polypeptides, for example, in order to measure the level of cIAP1 or cIAP2 polypeptide in the sample. The sample can be from a patient at any stage of disease, for example, a patient with early stage prostate cancer. In addition, the level of these biomarkers can be used in combination with the levels of other markers such as the level of apoptotic polypeptides or other diagnostic markers. As with the method described further above for using the level of XIAP to determine a prognosis for survival for a patient with a prostate neoplastic condition, the method can be used to determine if the patient is at risk for relapse or to determine the proper course of treatment for the patient.

As disclosed herein (see Example I), elevated levels of cIAP2 were found in 73% (11/15) of prostate cancer patients that developed metastatic disease compared to only 35% (16/46) of patients that remained free of disease ($p=0.009$). Therefore, an increased level of cIAP2 in a sample from a patient with a prostate neoplastic condition correlates with increased chance of prostate tumor metastasis.

As disclosed herein (see Example I), when stepwise multivariate analyses were conducted with backward elimination in the Cox proportional hazard regression model, the factors most predictive of relapse were cIAP2 and the Gleason score. The high cIAP2 and high Gleason score (8-10) increased risk of prostate cancer recurrence 3.7-fold ($p=0.008$) and 3.1-fold ($p=0.02$), respectively. Therefore, increased level of cIAP2 in said sample can correlate with increased chance of recurrence of a prostate neoplastic condition. In addition to measuring the level of cIAP2 in a sample from a patient with a prostate neoplastic condition, the Gleason score for that patient can be obtained, where a high Gleason score correlates with increased chance of recurrence of disease.

Tumor recurrence refers to further growth of neoplastic or cancerous prostate cells after diagnosis of prostate cancer. Particularly, recurrence can occur when further cancerous cell growth occurs in the cancerous tissue. Tumor spread refers to dissemination of prostate cancer cells into local or distant tissues and organs, for example during tumor metastasis.

The Gleason score is a measurement of the level of differentiation of cells in a prostate neoplastic cell-containing sample from a prostate cancer patient. The pathologist examines two biopsy samples each taken from a different area of the tumor and assigns to each a score of 1 to 5, based on the degree of cell differentiation. The more abnormal the tissue, the higher the score. The sum of the two scores produces the Gleason score. Scores of 2 to 4 indicate that the cells are well differentiated, meaning the tissue is not too abnormal; 5 to 7 moderately differentiated; 8 to 10 poorly differentiated. A high score such as 8, 9, or 10, correlates with increased chance of recurrence of disease (see Example I).

The invention also provides a method of determining a prognosis for survival for a patient with a prostate neoplastic condition, by (a) measuring the level of two or more IAPs selected from the group consisting of XIAP, cIAP1, and cIAP2 in a neoplastic prostate cell-containing sample from a patient, and (b) comparing the level of the two or more IAPs in the sample to a reference level of the IAPs, where an increased level of XIAP and decreased level of any of cIAP1 or cIAP2 in the sample correlates with increased survival of the patient.

The methods of the invention can be practiced, for example, by selecting two or more biomarkers, two biomarkers for which increased expression correlates with improved survival; two biomarkers for which decreased expression correlates with improved survival; one biomarker for which increased expression correlates with improved survival together with a biomarker for which decreased expression correlates with improved survival; or a any of XIAP, cIAP1, or cIAP2, with a known or standard biomarker for a prostate neoplastic condition, such as PSA, or with a known apoptotic protein such as Bcl-2. Similarly, three or more, four or more or five or more or a multitude of biomarkers can be used together for determining a prognosis for survival for a patient with a prostate neoplastic condition.

The use of two or more biomarkers can provide increased confidence in prognostic outcome. Those skilled in the art will recognize that such correlations can be observed using other combinations of biomarkers using methods described herein. For example, polypeptides known to be involved in apoptosis such as Bcl-2, Bax, Apaf1, Bid, Bcl-XL, Bcl-XS, Smac and TUCAN among others can be using in combination with the disclosed IAP biomarkers.

Figure 3:
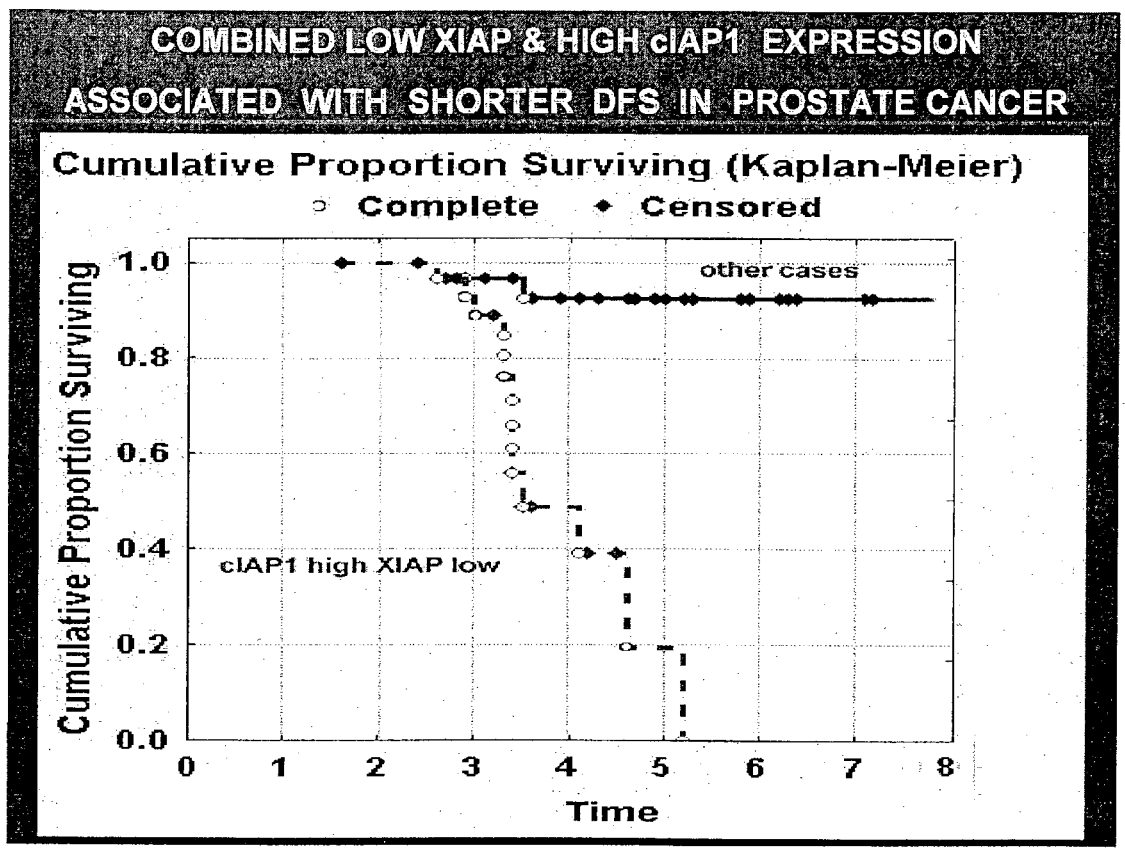
FIG. 3 shows Kaplan-Meier curves for low XIAP and high cIAP1 expression associated with shorter disease-free survival in prostate cancer patients.

As with the method described further above for using the level of XIAP, cIAP1, or cIAP2 individually to determine a prognosis for survival for a patient with a prostate neoplastic condition, this method using two or more IAPs can be used to determine overall survival or disease-free survival. The sample used for measurement can be, for example prostate tissue or a fluid such as blood, serum, urine, or semen. Measurement of the level of the IAP biomarkers can be performed, for example, using an antibody specifically reactive with these polypeptides, for example, in order to measure the level of IAP biomarker polypeptide in the sample. The two or more IAPs measured can be, for example, XIAP and cIAP2, or XIAP and cIAP1, or cIAP1 and cIAP2, or XIAP, cIAP1, and cIAP2. For example, FIG. 3 shows that low XIAP and high cIAP1 levels are correlated with shorter disease-free survival in prostate cancer patients. The sample used in the methods of the invention can be from a patient at any stage of disease, for example, a patient with early stage prostate cancer. As with the method described further above for using the level of XIAP, cIAP1, or cIAP2 to determine a prognosis for survival for a patient with a prostate neoplastic condition, this method can be used to determine if the patient is at risk for relapse or to determine the proper course of treatment for the patient.

Patients having a prostate neoplastic condition can be classified according to whether a high level of a particular biomarker, or a low level of the biomarker, is measured in a neoplastic prostate cell-containing sample obtained from the patient. Determination of the prognosis for the patient can be made by determining whether the group to which the patient has been assigned correlates with a higher or lower likelihood of disease-free or overall survival with respect to the group to which the patient was not assigned.

Therefore, the invention provides a method of determining a prognosis for survival for a patient with a prostate neoplastic condition, by (a) measuring a level of an IAP selected from the group consisting of XIAP, cIAP1, and cIAP2 in a neoplastic cell-containing sample from a patient, and (b) classifying the patient as belonging to either a first or second group of patients, wherein the first group of patients having a high level of an IAP is classified as having a different likelihood of suffering prostate disease recurrence or spread than the second group of patients having a low level of an IAP. For example, the first group of patients having a high level of XIAP can be classified as having a decreased risk of prostate tumor recurrence or spread compared to a second group of patients having a low level of XIAP. In addition, the first group of patients having a high level of cIAP1 or cIAP2 can be classified as having an increased risk of prostate tumor recurrence or spread compared to a second group of patients having a low level of cIAP1 or cIAP2.

As with the method described further above for using the level of XIAP, cIAP1, or cIAP2 to determine a prognosis for survival for a patient with a prostate neoplastic condition, this classification method can be used to determine overall survival or disease-free survival. The sample used for measurement can be, for example prostate tissue or a fluid such as blood, serum, urine, or semen. Measurement of the level of XIAP, cIAP1 or cIAP2 can be performed, for example, using an antibody specifically reactive with these polypeptides, for example, in order to measure the level of XIAP, cIAP1 or cIAP2 polypeptide in the sample. The sample can be from a patient at any stage of disease, for example, a patient with early stage prostate cancer. As with the method described further above for using the level of XIAP, cIAP1, or cIAP2 to determine a prognosis for survival for a patient with a prostate neoplastic condition, the method can be used to determine if the patient is at risk for relapse or to determine the proper course of treatment for the patient.

In one embodiment of the invention, it has been discovered that overproduction or a high level of cIAP2 correlates with patients having an increased risk of disease recurrence or spread. Thus, in this embodiment, patients belonging to a first group having high levels of cIAP2 are classified as having an increased risk of disease recurrence or spread compared to a second group of patients having low levels of cIAP2.

After the levels of a biomarker in patient sample have been determined and compared to a reference level, the patient is then classified into a group having a certain likelihood of disease free or overall survival. Then the likelihood of disease-free or overall survival for the patient is assessed based on the likelihood of disease-free or overall survival for patients in that group. For example, a neoplastic cell containing sample from a prostate cancer patient can be determined to have high levels of XIAP relative to a reference level. This patient would then be classified into a group of patients having high levels of XIAP. Since, in accordance with the present invention, it has been discovered that there is an increased likelihood of disease-free or overall survival for the group of patients expressing high levels of XIAP in neoplastic prostate cells (relative to those expressing low levels of XIAP), the specific prostate cancer patient would be considered to have an increased likelihood of disease free or overall survival.

Conversely, for example, a neoplastic prostate cell containing sample from a prostate cancer patient can be determined to have high levels of cIAP1 or cIAP2 relative to a reference level. This patient would then be classified into a group of patients having high levels of cIAP1 or cIAP2. Since, in accordance with the present invention, it has been discovered that there is a decreased likelihood of disease-free or overall survival for the group of patients expressing high levels of cIAP1 or cIAP2 in neoplastic prostate cells (relative to those expressing low levels of cIAP1 or cIAP2), the specific prostate cancer patient would be considered to have an decreased likelihood of disease free or overall survival.

The methods of the invention are also applicable to determining the susceptibility of an individual for developing a prostate neoplastic condition. Subjects who may or may not be at risk for developing a prostate neoplastic condition can be screened for the presence of IAP levels in a sample of prostate cells from the subject.

The methods of the invention are applicable for use with a variety of different types of samples isolated or obtained from an individual having, or suspected of having a prostate neoplastic condition. For example, samples applicable for use in one or more prognostic formats of the invention, include tissue and cell samples. A tissue or cell sample can be obtained, for example, by biopsy or surgery. For example, in the case of solid tumors which have not metastasized, a tissue sample from the surgically removed tumor can be obtained and prepared for testing by conventional techniques.

As described below, and depending on the format of the method, the tissue can be used whole or subjected to various methods known in the art to disassociate the sample into smaller pieces, cell aggregates or individual cells. Additionally, when combined with amplification methods such as polymerase chain reaction (PCR), a single prostate cell sample is sufficient for use in prognostic assays of the invention which employ hybridization detection methods. Similarly, when measuring biomarker polypeptide levels, amplification of the signal with enzymatic coupling or photometric enhancement can be employed using only a few or a small number of cells.

Whole tissue obtained from a prostate biopsy or surgery is one example of a prostate cell sample. Whole tissue prostate cell samples can be assayed employing any of the formats described below. For example, the prostate tissue sample can be mounted and hybridized in situ with biomarker nucleic acid probes. Similar histological formats employing polypeptide detection methods and in situ activity assays also can be used to detect a biomarker polypeptide in whole tissue prostate cell samples. Polypeptide detection methods include, for example, staining with a biomarker specific antibody, as described herein, in Example I. Such histological methods as well as others well known to those skilled in the art are applicable for use in the prognostic methods of the invention using whole tissue as the source of a prostate cell sample. Methods for preparing and mounting the samples are similarly well known in the art.

Individual prostate cells and cell aggregates from an individual having, or suspected of having a prostate neoplastic condition or prostate cancer is another example of a prostate cell sample which can be analyzed for increased expression of biomarker RNA or polypeptide. The cells can be grown in culture and analyzed using procedures such as those described above. Whole cell samples expressing cell surface markers associated with biomarker expression can be rapidly tested using fluorescent or magnetic activated cell sorting (FACS or MACS) with labeled binding agents selective for the surface marker or using binding agents selective for epithelial or prostate cell populations, for example, and then determining a test expression level of a biomarker within this population. A level of a biomarker can be determined using, for example, binding specifically reacting agents for a biomarker or by hybridization to a biomarker specific probe. Other methods for measuring the level of a biomarker in whole cell samples are known in the art and are similarly applicable in any of the prognostic formats described below.

The tissue or whole cell prostate cell sample obtained from an individual also can be analyzed for increased or decreased biomarker levels by lysing the cell and measuring the level of a biomarker in the lysate, a fractionated portion thereof or a purified component thereof using any of formats described herein. For example, if a hybridization format is used, biomarker RNA can be amplified directly from the lysate using PCR, or other amplification procedures well known in the art such as RT-PCR, 5' or 3' RACE to directly measure the level of a biomarker nucleic acid molecules. RNA also can be isolated and probed directly such as by solution hybridization or indirectly by hybridization to immobilized RNA. Similarly, when determining a level of a biomarker using polypeptide detection formats, lysates can be assayed directly, or they can be further fractionated to enrich for a biomarker. For example, an immunochemical method, such as immunoblot analysis (see Example I) can be performed using a neoplastic cell-containing sample. Numerous other methods applicable for use with whole prostate cell samples are well known to those skilled in the art and can accordingly be used in the methods of the invention.

The prostate tissue or cell sample can be obtained directly from the individual or, alternatively, it can be obtained from other sources for testing. Similarly, a cell sample can be tested when it is freshly isolated or it can be tested following short or prolonged periods of cryopreservation without substantial loss in accuracy or sensitivity. If the sample is to be tested following an indeterminate period of time, it can be obtained and then cryopreserved, or stored at 4° C. for short periods of time, for example. An advantage of the prognostic methods of the invention is that they do not require histological analysis of the sample. As such, the sample can be initially disaggregated, lysed, fractionated or purified and the active component stored for later diagnosis.

The prognostic methods of the invention are applicable for use with a variety of different types of samples other than prostate cell samples. For example, a biomarker polypeptide or fragment thereof that is released into the extracellular space, including circulatory fluids as well as other bodily fluids, can be used in prognostic methods to detect a secreted polypeptide or fragment related to a biomarker polypeptide. In such a case, the methods of the invention are applicable with fluid samples collected from an individual having, or suspected of having a prostate neoplastic condition or prostate cancer.

Fluid samples, which can be measured for biomarker levels, include, for example, blood, serum, lymph, urine and semen. Other bodily fluids are known to those skilled in the art and are similarly applicable for use as a sample in the prognostic methods of the invention. One advantage of analyzing fluid samples is that they are readily obtainable, in sufficient quantity, without invasive procedures as required by biopsy and surgery. Analysis of fluid samples such as blood, serum and urine will generally be in the prognostic formats described herein which measure biomarker polypeptide levels. As the biomarker related polypeptide is circulating in a soluble form, the methods will be similar to those which measure expression levels from cell lysates, fractionated portions thereof or purified components.

Prostate neoplastic conditions can be diagnosed, predicted or prognosed by measuring a level of a biomarker in a prostate cell sample, circulating fluid or other bodily fluid obtained from the individual. As described herein, levels of a biomarker can be measured by a variety methods known in the art.

One skilled in the art can readily determine an appropriate assay system given the teachings and guidance provided herein and choose a method based on measuring RNA or polypeptide. Considerations such as the sample type, availability and amount will also influence selection of a particular prognostic format. For example, if the sample is a prostate cell sample and there is only a small amount available, then prognostic formats which measure the amount of biomarker RNA by, for example, PCR amplification, or which measure biomarker polypeptide by, for example, FACS analysis can be appropriate choices for determining the level of a biomarker. Alternatively, if the sample is a blood sample and the user is analysing numerous different samples simultaneous, such as in a clinical setting, then a multisample format, such as an Enzyme Linked Immunoabsorbant Assay (ELISA), which measures the amount of a biomarker polypeptide can be an appropriate choice for determining the level of a biomarker. Additionally, biomarker nucleic acid molecules released into bodily fluids from the neoplastic or pathological prostate cells can also be analyzed by, for example, PCR or RT-PCR. Those skilled in the art will know, or can determine which format is amenable for a particular application and which methods or modifications known within the art are compatible with a particular type of format.

Nucleic acid probes can be produced recombinantly or chemically synthesized using methods well known in the art. Additionally, hybridization probes can be labeled with a variety of detectable labels including, for example, radioisotopes, fluorescent tags, reporter enzymes, biotin and other ligands. Such detectable labels can additionally be coupled with, for example, calorimetric or photometric indicator substrate for spectrophotometric detection. Methods for labeling and detecting such probes are well known in the art and can be found described in, for example, Sambrook et al., *Molecular Cloning: A Laboratory Manual,* 2nd ed., Cold Spring Harbor Press, Plainview, N.Y. (1989), and Ausubel et al., *Current Protocols in Molecular Biology* (Supplement 47), John Wiley & Sons, New York (1999).

Nucleic acid probes useful for detecting a biomarker in a sample can be hybridized under various stringency conditions readily determined by one skilled in the art. Depending on the particular assay, one skilled in the art can readily vary the stringency conditions to optimize detection of a particular biomarker in a particular sample type.

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, at least 75% identity, at least 85% identity; or at least 90% identity. Moderately stringent conditions are conditions equivalent to hybridization in 50% formamide, 5×Denhart's solution, 5×SSPE, 0.2% SDS at 42° C., followed by washing in 0.2× SSPE, 0.2% SDS, at 42° C. High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C.

Low stringency hybridization refers to conditions equivalent to hybridization in 10% formamide, 5×Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art and are described, for example, in Sambrook et al., *Molecular Cloning: A Laboratory Manual*, 2nd ed., Cold Spring Harbor Press, Plainview, N.Y. (1989); and Ausubel et al., supra, 1999). Nucleic acid molecules encoding polypeptides hybridize under moderately stringent or high stringency conditions to substantially the entire sequence, or substantial portions, for example, typically at least 15-30 nucleotides of the nucleic acid sequences of XIAP, cIAP1 or cIAP2 or another biomarker.

Any of the methods described above using individual IAP levels or combinations of IAP levels to determine a prognosis for survival for a patient with a prostate neoplastic condition can be used alone or in combination with other diagnostic tests or markers of prostate neoplastic diseases. Other diagnostic tests or markers can be non-IAP markers such as PSA level or the level of an apoptotic polypeptide such as Bcl-2. In addition, methods directed to correlations with disease recurrence or tumor metastasis can be used alone or in combination with other diagnostic tests or markers of prostate neoplastic diseases.

Several tests and markers are used to help diagnose, for example, prostate cancer. Tests include digital rectal examination (DRE) where a physician inserts a gloved finger into the rectum to feel the surface of the prostate gland. Healthy prostate tissue is soft and fleshy while malignant tissue is firm, hard, and often asymmetrical or stony. Only larger tumors can be felt; and as many as one-third of patients subsequently diagnosed with prostate cancer have a normal DRE. Another diagnostic test is transrectal ultrasound (TRUS) imaging which is used to measure the size of the prostate and to detect and analyze cancerous tumors. A special probe is inserted through the rectum and projects ultrasonic impulses against the prostate. The results are viewed on a monitor, enabling the physician to obtain a visual image of the gland, surrounding tissue, and any tumor. Not all cancers can be detected ultrasonically, however, so TRUS can be performed in conjunction with a digital rectal exam (DRE).

A common diagnostic test for prostate neoplastic conditions is the prostate-specific antigen (PSA) test. Prostate-specific antigen is produced by the cells of the prostate capsule and periurethral glands. The test measures the amount of PSA in the blood. The PSA level is related in part to the size and weight of the prostate. Patients with benign prostatic hyperplasia (BPH) or prostatitis produce increased amounts of PSA. For these reasons, some refinements the PSA test have been developed. The PSA test can produce false positive and false negative results. A false positive result occurs when the PSA level is elevated and there is no cancer. A false negative result occurs when there is cancer but the PSA level is normal.

PSA in the blood can be bound molecularly to a variety of serum proteins or can exist in a free, or unbound, state. Total PSA is the sum of both forms; free PSA constitutes the unbound PSA only. Studies suggest that malignant prostate cells produce more bound PSA. Therefore, a low proportion of free PSA in relation to total PSA may indicate a cancerous prostate, and a high proportion of free PSA may indicate a normal prostate, BPH, or prostatitis.

PSA is measured in nanograms per milliliter (ng/mL). A PSA of 4 ng/mL or lower is normal; 4-10 ng/mL is slightly elevated; and 10-20 moderately elevated. Most men with slightly elevated PSA levels do not have prostate cancer, and many men with prostate cancer have normal PSA levels. PSA level can increase with age. A PSA of up to 2.5 ng/mL for men age 40-49 is considered normal, as are 3.5 ng/mL for men age 50-59, 4.5 ng/mL for men age 60-69, and 6.5 ng/mL for men 70 and older. The rate of change in PSA over time is termed PSA velocity (PSAV). PSAV of 0.75 ng/mL/yr or higher can indicate significant prostate cancer. Therefore, a man with a PSA of 4-10 ng/mL, who has a PSAV of 0.75 ng/mL/yr may have a cancerous prostate condition.

Prostatic acid phosphatase is an enzyme produced by prostate tissue that contributes to seminal fluid. Its production increases as prostate disease progresses. The PAP test can be used with other tests to detect and monitor advanced prostate cancer.

A prostate biopsy can be performed to determine the type of cancer, its location, and stage of development. A biopsy needle, similar to those used to draw blood or administer injections, is inserted through the perineum into the tumor; or a probe, guided by transrectal ultrasound (TRUS), is inserted into the rectum. The needle is projected into the tumor through the tip of the probe, and a cell sample is extracted from one or several areas of the tumor into the syringe.

The methods of the invention can also be used for diagnosing a prostate neoplastic condition in a male subject. The methods are based on comparison of the level of one or more IAP biomarkers in a neoplastic prostate cell-containing sample from a subject to a reference level of the biomarker. For example, the reference level can be determined from a non-neoplastic prostate cell-containing sample from the same subject or from a group of subjects. An IAP biomarker level that is diagnostic of a prostate neoplastic condition, for example, the level of cIAP2, can be used to screen subjects for prostate neoplastic conditions. Subjects may or may not be at risk for, or be suspected of having, a prostate neoplastic condition. The IAP biomarker level can be used alone or in combination with other diagnostic markers to diagnose a prostate neoplastic condition in a subject.

As disclosed herein (see Example I), cIAP2 immunoscores were significantly higher in advanced prostate cancers, as defined by clinical stage (stage A vs stage B-C; stage A vs. stage D: p, 0.0001). The invention also provides a method of determining the stage of prostate cancer in a prostate cancer patient. The method consists of (a) obtaining a neoplastic prostate cell-containing sample from a prostate cancer patient, (b) measuring the level of cIAP2 in the sample, and (c) comparing the level of cIAP2 in the sample to a reference level of cIAP2, where increased levels of cIAP2 in the sample correlate with advanced prostate cancer. The advanced prostate cancer can be stage B, C, and D, for example, where advanced prostate cancer is stage D. This method can be used alone or in combination with other staging systems, for example, the Jewett system.

The invention relates to the discovery that increased or decreased amounts of particular biomarkers, including XIAP, cIAP1, or cIAP2, are predictive of survival of patients having a prostate neoplastic condition. The over-expression or under-expression of these biomarkers can contribute to the genetic malfunction of neoplastic cells that leads to uncontrolled proliferation. Therefore, modulation of the level of a biomarker in a neoplastic cell to a level consistent with a normal cell can be used to return a neoplastic cell to a more normal proliferation state. In the case of over-expressed biomarker genes, such as cIAP1 or cIAP2 a variety of strategies can be employed to reduce gene expression. For example, inhibition of transcription or translation of cIAP1 or cIAP2, or reduction in the amount of active cIAP1 or cIAP2 polypeptide, can be used to reduce the levels of these biomarkers to a level representative of a normal cell. In the case of under-expressed biomarker genes, such as XIAP, a variety of strategies can be employed to increase gene expression. For example, introduction of XIAP from an exogenous nucleic acid molecule, promotion of transcription or translation of XIAP, or promotion in the amount of active XIAP polypeptide, can be used to increase the levels of these biomarkers to a level representative of a normal cell.

Therefore, the invention additionally provides a method for treating or reducing the progression of a prostate neoplastic condition such as prostate cancer by reducing neoplastic prostate cell proliferation. In one embodiment, the method involves administering a nucleic acid encoding XIAP into a neoplastic prostate cell and expressing the XIAP polypeptide in an amount effective to reduce neoplastic cell proliferation. In another embodiment, the method of reducing neoplastic prostate cell proliferation involves contacting a neoplastic prostate cell with an effective amount of an agent that, under sufficient conditions, increases the amount of XIAP in the cell.

An agent includes, for example, a polypeptide, peptidomimetic, non-peptidyl compound, carbohydrate, lipid, an antibody or antibody fragment, a small organic or inorganic molecule, or a nucleotide sequence including an aptamer. For example, an agent can be a small organic compound obtained from a combinatorial chemical library. In addition, for example, an agent can be a ribozyme, an antisense oligonucleotide, or a nucleotide sequence that encodes a polypeptide. An agent can have a known or unknown structure so long as it has the intended activity.

Such an agent can increase the amount of a biomarker directly or indirectly, for example, by increasing the amount of a biomarker polypeptide in a cell, such as by stimulating increased mRNA expression. XIAP mRNA expression can be increased, for example, by inducing or derepressing transcription of XIAP genes and by regulating the expression of a cellular protein that acts as a transcription factor to regulate gene expression. An agent can act to increase the amount of XIAP by increasing the stability of a XIAP mRNA or polypeptide, for example, by decreasing a cellular degradation activity, such as a protease activity. Molecules that mediate the regulation of XIAP expression, such as receptors and corresponding signal transduction molecules, can also be targets of agents that increase the amount of XIAP in a cell. For example, a signal transduction pathway that stimulates the expression of XIAP can be modulated to increase the level of XIAP expression, for example, by increasing the rate of XIAP synthesis or the length of time that gene expression remains active.

Conversely, a decrease in the amount of a biomarker in a cell can be affected by inducing changes in biomarker transcription, translation or protein stability opposite to those described above. As such, in a further embodiment, the method of reducing neoplastic prostate cell proliferation involves contacting a neoplastic prostate cell with an effective amount of an agent that, under sufficient conditions, decreases the amount of cIAP1 or cIAP2 in the cell.

The amount of a biomarker in a cell, such as cIAP1 or cIAP2, can be modulated, for example, by increasing expression of the biomarker from an exogenous nucleic acid molecule, by introducing a biomarker polypeptide or functional analog thereof into a cell, by introducing inhibitor of a biomarker polypeptide into a cell, and by modulating the expression or activity of a gene or protein product that regulates the level of a biomarker in a cell. The amount of a biomarker in a cell also can be modulated using an antisense molecule to block transcription or translation of the biomarker mRNA. Specifically, cells can be transformed with sequences complementary to cIAP1 or cIAP2 nucleic acid molecules. Such methods are well known in the art, and sense or antisense oligonucleotides or larger fragments, can be designed from various locations along the coding or control regions of sequences encoding biomarkers. Thus, antisense molecules can be used to modulate biomarker activity, or to achieve regulation of gene function.

Ribozymes, enzymatic RNA molecules, can also be used to catalyze the specific cleavage of a biomarker mRNA, such as cIAP1 or cIAP2. The mechanism of ribozyme action involves sequence-specific hybridization of the ribozyme molecule to complementary target biomarker RNA, followed by endonucleolytic cleavage. Specific ribozyme cleavage sites within any potential RNA target are identified by scanning the biomarker RNA for ribozyme cleavage sites which include the following sequences: GUA, GUU, and GUC. Once identified, short RNA sequences of between 15 and 20 ribonucleotides corresponding to the region of the target gene containing the cleavage site can be evaluated for secondary structural features which can render the oligonucleotide inoperable. The suitability of candidate targets can also be evaluated by testing accessibility to hybridization with complementary oligonucleotides using ribonuclease protection assays. Antisense molecules and ribozymes of the invention can be prepared by any method known in the art for the synthesis of nucleic acid molecules.

A variety of methods are known in the art for introducing a nucleic acid molecule into a cell, including a cancer cell. Such methods include microinjection, electroporation, lipofection, calcium-phosphate mediated transfection, DEAE-Dextran-mediated transfection, polybrene- or polylysine-mediated transfection, and conjugation to an antibody, gramacidinS, artificial viral envelopes or other intracellular carriers such as TAT. For example, cells can be transformed by microinjection as described in Cibelli et al., Nat. Biotech. 16:642-646 (1998) or Lamb and Gearhart, Cur. Opin. Gen. Dev. 5:342-348 (1995); by lipofection as described in Choi (U.S. Pat. No. 6,069,010) or Lamb and Gearhart, Cur. Opin. Gen. Dev. 5:342-348 (1995); by electroporation as described in Current Protocols in Molecular Biology, John Wiley and Sons, pp 9.16.4-9.16.11 (2000) or Cibelli et al., Nat. Biotech. 16:642-646 (1998); or by fusion with yeast spheroplasts Lamb and Gearhart, Cur. Opin. Gen. Dev. 5:342-348 (1995).

A nucleic acid encoding a biomarker polypeptide, such as XIAP, or other molecule useful for reducing proliferation of a prostate cancer cell, can be delivered into a mammalian cell, either in vivo or in vitro using suitable vectors well-known in the art. Suitable vectors for delivering a nucleic acid encoding a biomarker polypeptide to a mammalian cell, include viral vectors and non-viral vectors such as plasmid vectors. Such vectors are useful for providing therapeutic amounts of a biomarker polypeptide, such as XIAP, as well as for delivering antisense nucleic acid molecules and ribozymes.

Viral based systems provide the advantage of being able to introduce relatively high levels of the heterologous nucleic acid into a variety of cells. Suitable viral vectors for introducing a nucleic acid encoding a biomarker polypeptide, such as XIAP, into a mammalian cell are well known in the art. These viral vectors include, for example, Herpes simplex virus vectors (Geller et al., Science, 241:1667-1669 (1988)); vaccinia virus vectors (Piccini et al., Meth. Enzymology, 153:545-563 (1987)); cytomegalovirus vectors (Mocarski et al., in Viral Vectors, Y. Gluzman and S. H. Hughes, Eds., Cold Spring Harbor Laboratory, Cold Spring Harbor, N.Y., 1988, pp. 78-84)); Moloney murine leukemia virus vectors (Danos et al., Proc. Natl. Acad. Sci. USA, 85:6460-6464 (1988); Blaese et al., Science, 270:475-479 (1995); Onodera et al., J. Virol., 72:1769-1774 (1998)); adenovirus vectors (Berkner, Biotechniques, 6:616-626 (1988); Cotten et al., Proc. Natl. Acad. Sci. USA, 89:6094-6098 (1992); Graham et al., Meth. Mol. Biol., 7:109-127 (1991); Li et al., Human Gene Therapy, 4:403-409 (1993); Zabner et al., Nature Genetics, 6:75-83 (1994)); adeno-associated virus vectors (Goldman et al., Human Gene Therapy, 10:2261-2268 (1997); Greelish et al., Nature Med., 5:439-443 (1999); Wang et al., Proc. Natl. Acad. Sci. USA, 96:3906-3910 (1999); Snyder et al., Nature Med., 5:64-70 (1999); Herzog et al., Nature Med., 5:56-63 (1999)); retrovirus vectors (Donahue et al., Nature Med., 4:181-186 (1998); Shackleford et al., Proc. Natl. Acad. Sci. USA, 85:9655-9659 (1988); U.S. Pat. Nos. 4,405,712, 4,650, 764 and 5,252,479, and WIPO publications WO 92/07573, WO 90/06997, WO 89/05345, WO 92/05266 and WO 92/14829; and lentivirus vectors (Kafri et al., Nature Genetics, 17:314-317 (1997)). It is understood that both permanent and transient expression can be useful in a method of the invention.

An XIAP polypeptide-encoding recombinant nucleic acid can be directed into a particular tissue or organ system, for example, by vector targeting or tissue-restricted gene expression. Therefore, a vector useful for therapeutic administration of a nucleic acid encoding an XIAP polypeptide can contain a regulatory element that provides tissue specific expression of the polypeptide. For example, a nucleic acid sequence encoding a XIAP polypeptide can be operatively linked to a prostate cell specific promoter.

Any of a variety of inducible promoters or enhancers can also be included in a nucleic acid or vector of the invention to allow control of expression of a XIAP polypeptide, or another molecule useful for modulating cell proliferation, such as an antisense nucleic acid molecule or ribozyme, by added stimuli or molecules. Such inducible systems, include, for example, tetracycline inducible system (Gossen & Bizard, Proc. Natl. Acad. Sci. USA, 89:5547-5551 (1992); Gossen et al., Science, 268:1766-1769 (1995); Clontech, Palo Alto, Calif.); metalothionein promoter induced by heavy metals; insect steroid hormone responsive to ecdysone or related steroids such as muristerone (No et al., Proc. Natl. Acad. Sci. USA, 93:3346-3351 (1996); Yao et al., Nature, 366:476-479 (1993); Invitrogen, Carlsbad, Calif.); mouse mammory tumor virus (MMTV) induced by steroids such as glucocortocoid and estrogen (Lee et al., Nature, 294:228-232 (1981); and heat shock promoters inducible by temperature changes.

An inducible system particularly useful for therapeutic administration utilizes an inducible promoter that can be regulated to deliver a level of therapeutic product in response to a given level of drug administered to an individual and to have little or no expression of the therapeutic product in the absence of the drug. One such system utilizes a Gal4 fusion that is inducible by an antiprogestin such as mifepristone in a modified adenovirus vector (Burien et al., Proc. Natl. Acad. Sci. USA, 96:355-360 (1999). The GENE SWITCH inducible expression system (U.S. Pat. Nos. 5,935,934 and 5,874,534) is an example of such a system. Other inducible systems use the drug rapamycin to induce reconstitution of a transcriptional activator containing rapamycin binding domains of FKBP12 and FRAP in an adeno-associated virus vector (Ye et al., Science, 283:88-91 (1999)), use tetracycline to control transcription (Baron Nucleic Acids Res. 25:2723-2729 (1997)) and use synthetic dimerizers to regulate gene expression (Pollock et al., Methods Enzymol. 306:263-281 (1999)). Such a regulatable inducible system is advantageous because the level of expression of the therapeutic product can be controlled by the amount of drug administered to the individual or, if desired, expression of the therapeutic product can be terminated by stopping administration of the drug.

In accordance with another embodiment of the present invention, there are provided diagnostic and prognostic systems, preferably in kit form, comprising at least one IAP biomarker antibody or nucleic acid probe in a suitable packaging material. A suitable diagnostic system includes at least one antibody or nucleic acid probe, as a separately packaged chemical reagent(s) in an amount sufficient for at least one assay. A kit can contain a reaction cocktail that provides the proper conditions for performing an assay, for example, an ELISA or other immunoassay, for determining the level of expression of IAP polypeptides or nucleic acids in a sample. In addition a kit can contain control samples that contain known amounts of IAP polypeptides or nucleic acids and, if desired, a second antibody specific for the primary antibody.

The contents of the kit are contained in packaging material, preferably to provide a sterile, contaminant-free environment. In addition, the packaging material contains instructions indicating how the materials within the kit can be employed both to detect the presence or absence or level of a particular IAP biomarker or to diagnose the presence of, or a predisposition for a prostate neoplastic. The instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

It is understood that modifications which do not substantially affect the activity of the various embodiments of this invention are also included within the definition of the invention provided herein. Accordingly, the following examples are intended to illustrate but not limit the present invention.

Example I

Expression of Inhibitor of Apoptosis (IAP) Polypeptides in Prostate Cancer

This example shows a method for identifying biomarkers that correlate to prostate cancer patient survival. A study was performed for IAP-family members on needle biopsy specimens for a cohort of 62 men with stage II peripheral zone prostate carcinomas treated by external beam irradiation. Stage II disease is also known as stage B (B0, B1, B2 combined) disease. Cancer progression during a median follow-up of 66 months was defined as biochemical recurrence (3 consecutive rises in prostate specific antigen (PSA) concentration). Of 16/62 (26%) patients classified as alive with disease (AWD) with regard to biochemical failure, 15 patients developed metastatic disease documented by bone scans.

Figure 2:
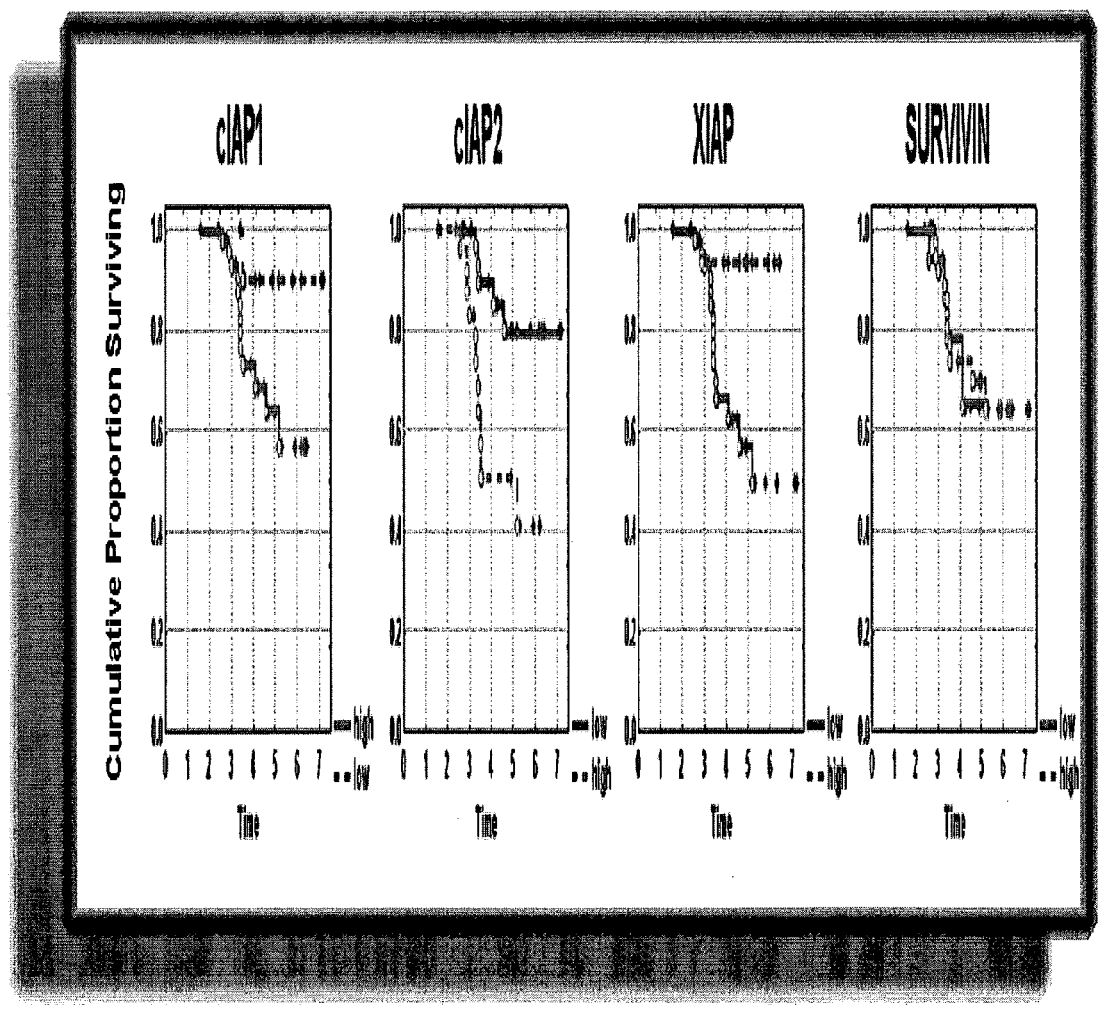
FIG. 2 shows Kaplan-Meier curves for cIAP1, cIAP2, XIAP, and Survivin immunoscores with disease-free survival of a cohort of prostate cancer patients.

Briefly, 62 adenocarcinoma specimens and 40-48 case-matched samples containing normal prostatic epithelium were immunostained and evaluated for the presence of cIAP1, cIAP2, XIAP, and Survivin polypeptides. The mean intensity of immunostaining was significantly higher in invasive cancer as compared to normal prostatic epithelium for all the investigated polypeptides. To analyze the relationship of biomarkers to patient survival, comparisons of the immunoscores obtained for normal prostatic epithelium and prostate cancers were used to set logical cut-off values for the dichotomization of data (see FIG. 1). Kaplan-Meier curves and log rank tests demonstrated statistically significant associations of cIAP1, cIAP2, and XIAP with disease-free survival (DFS). Interestingly, while higher levels of cIAP1 and cIAP2 were associated with shorter DFS (p=0.05 and p=0.006, respectively), higher XIAP levels were unexpected correlated with longer DFS (p=0.02) (see FIG. 2).

Elevated levels of cIAP2 were found in 11/15 (73%) of prostate cancer patients that developed metastatic disease compared to only 16/46 (35%) of patients that remained free of disease (p=0.009). In contrast to cIAP2, high levels of XIAP were found in only 1/15 (7%) of patients who developed metastatic disease, but also a relatively small portion of patients who remained free of metastatic disease contained elevated XIAP in their tumors (14/46[30%]). Furthermore, low levels of XIAP protein were associated with high PSA (mean 26.4 ng/ml; Hybritech assay) compared with tumors highly positive for XIAP (mean PSA 11.7 ng/ml) (p=0.009). Low XIAP levels combined with high cIAP1 levels were correlated with shorter DFS in prostate cancer patients (see FIG. 3).

When stepwise multivariate analyses were conducted with backward elimination in the Cox proportional hazard regression model, the factors most predictive of relapse were cIAP2 and the Gleason score. The high cIAP2 and high Gleason score (8-10) increased risk of prostate cancer recurrence 3.7-fold (p=0.008) and 3.1-fold (p=0.02), respectively.

A similar tendency was observed in a study of tissue arrays of 772 prostate cancer specimens containing 710 primary T1-T4 tumors and 62 metastases which were obtained from the archives of the University of Basel (Switzerland) and the Tampere University Hospital (Finland). cIAP2 immunoscores were significantly higher in advanced prostate cancers, as defined by clinical stage (stage A vs stage B-C; stage A vs stage D; p<0.0001). The 62 metastases collected at the autopsies from patients who had undergone androgen deprivation by orchiectomy and had subsequently died of end-stage metastatic prostate cancer, contained the highest levels of cIAP2 protein (median IS 200 in metastases vs median IS 80 in pT1 tumors, p<0.0001).

The SV40 T-antigen-transgenic mouse model of prostate cancer (TRAMP) which closely resembles the progression of human prostate cancer has been used to analyze the expression pattern of IAPs. Barely expressed in the normal prostatic epithelium, high levels of cIAP1 and cIAP2 proteins were displayed starting from BPH through PIN to adenocarcinoma with invasion of seminal vesicles (data not shown). While Survivin was not detected in the normal prostatic epithelium, and its rising levels in BPH, PIN, and well-differentiated tumors, declined in high grade adenocarcinomas (data not shown).

Methods:

Preparation and Characterization of Antibodies Useful for Detecting IAPs:

Antisera are raised against recombinant proteins and synthetic peptides for immunodetection of XIAP, cIAP1, and cIAP2. Prior to employing these antibodies for analysis of samples, the specificity of these antibodies for their intended protein targets is confirmed by SDS-PAGE/immunoblot analysis. For example, in vitro translated XIAP, cIAP1, and cIAP2 are subjected to SDS-PAGE/immunoblot analysis, using polyclonal XIAP antiserum (AR-27A). Incubation with XIAP antiserum detected only XIAP in vitro translated protein. Detergent lysates are prepared from various normal human tissues, normalized for total protein content (50 ug), and subjected to SDS-PAGE/immunoblot assay using antisera specific for XIAP, cIAP1, and cIAP2. In addition, lysates from matched pairs of carcinoma (T) and normal prostate (N) specimens are analyzed for total protein content (100 mg per lane) and subjected to SDS-PAGE/immunoblot analysis, using the antisera specific for XIAP, cIAP1, and cIAP2. Antibody detection is accomplished by an ECL method. Immunoblot data are quantified by scanning densitometry using Pro-Image software system.

The anti-XIAP antiserum reacted specifically with the expected ~57 kDa XIAP protein, but not with other IAP-family members including cIAP1, and cIAP2-which are all produced by in vitro transcription and translation from cDNAs. Anti-c-IAP1 and c-IAP2 antibodies were obtained from Santa Cruz Biotechnology Inc., CA and R&D Systems, Inc. Similarly, monospecificity of the anti-cIAP1 and anti-cIAP2 antiserum can be demonstrated by SDS-PAGE/immunoblot analysis.

Polyclonal antisera for IAPs are generated in rabbits using recombinant protein immunogens. For example, IAPs are produced as GST-fusion proteins from pGEX vectors using *Escherichia coli* BL21 (DE3) as the host strain. Additional anti-IAP serums are generated in rabbits using synthetic peptides as the immunogen. For example, a peptide can be synthesized with an N-terminal cysteine appended to permit conjugation to maleimide-activated carrier proteins KLH and OVA (Pierce, Inc.). This peptide conjugate can be used to generate a polyclonal antiserum in rabbits. Affinity-purified His 6-tagged-XIAP BIR2 recombinant protein can be produced using published methods and used as an immunogen to produce XIAP-specific antiserum. Other antibody serum can be produced in rabbits using a synthetic peptide. New Zealand white female rabbits are injected subcutaneously with a mixture of 0.25 ml KLH-peptide (1 mg/ml), 0.25 ml OVA-peptide (1 mg/ml), or recombinant protein (0.1-0.25 µg protein per immunization) and 0.5 ml Freund's complete adjuvant (dose divided over 10 injections sites) and then boosted 3 times at weekly intervals, followed by another 3-20 boostings at monthly intervals with 0.25 mg each of KLH-peptide, OVA-peptide, or recombinant protein immunogens in Freund's incomplete adjuvant, collecting blood at 1-3 weeks after each boosting to obtain immune serum.

Immunohistochemical Analysis of IAPs and Other Biomarkers in a Tissue Microarray A tissue microarray is constructed using primary tumor specimens derived from a cohort of prostate cancer patients. To construct prostate cancer microarrays, 2-5 cylinders of 1 mm diameter tissue are taken from representative areas of archival paraffin blocks containing 8% formalin-fixed tumor and arrayed into a new recipient paraffin block with a custom-built precision instrument (Beecher Instruments, Silver Spring, Md.). Serial sections (4 µm) are applied to 3-aminopropyl-triethoxysilane (APES)-coated slides (Sigma).

Microarrays are immunostained using antisera specific for the IAP family members XIAP, cIAP1, and cIAP2. The same procedure can be used for immunostaining other markers such as Apaf1, Smac, AIF, Bcl-2, Bcl-XL, Bax, BAG1, β-Catenin, MIB-1 and p53. Dewaxed tissue sections are immunostained using a diaminobenzidine (DAB)-based detection method as described in detail, employing the Envision-Plus-Horse Radish Peroxidase (HRP) system (DAKO) using an automated immunostainer (Dako Universal Staining System). Antisera specific for XIAP, cIAP1, and cIAP2 are applied at 1:3000 to 10000 (v/v). The dilutions of c-IAP1, c-IAP2 are 1:600 (v/v). For all tissues examined, the immunostaining procedure is performed in parallel using preimmune serum to verify specificity of the results. Initial confirmations of antibody specificity also include experiments in which antiserum is preabsorbed with 5-10 µg/ml of either synthetic peptide immunogen or recombinant protein immunogen. The scoring of tumor immunostaining is based on the percentage of immunopositive cells (0-100) multiplied by staining intensity score (0/1/2/3), yielding scores of 0-300. All immunostaining results are quantified according the approximate percentage of immunopositive cells (0-100%) and immunointensity on a 0-3 scale, and then an immunoscore is calculated from the product of the percentage immunopositivity and immunointensity (0-300).

Tissue sections are immunostained using various antisera, as described above, followed by detection using a HRPase-based method with diaminobenzidine calorimetric substrate (brown). Nuclei are counterstained with hematoxylin (blue).

Several of the tumor specimens on the array contained adjacent normal prostate tissue, permitting side-by-side comparisons of immunostaining results for normal versus malignant epithelium. Immunohistochemical analysis of tumor tissues on the microarray revealed several examples of cancer-specific alterations in the expression of these apoptosis-regulatory proteins.

Immunoblot Analysis of IAPs Frozen Prostate Cancer Specimens

To corroborate the immunohistochemistry data, frozen prostate cancer specimens are identified that had sufficient amounts of both adjacent normal (N) and tumor (T) tissue for immunoblot analysis using antibodies specific for IAPs or other proteins. Detergent-lysates of these tissues specimens are prepared and normalized for total protein content prior SDS-PAGE/immunoblot analysis. Densitometry analysis is also performed to quantify band intensities, and the results from the loading control blot are used to normalize all data.

Prostate cancer specimens with high ratios of cancer cells relative to stroma are selected for immunoblotting analysis. The protein lysates are prepared without additional microdissection or fractionation. The tumor lysates and the samples of the normal mucosa from the same patients are prepared using modified RIPA buffer (50 mM Tris [pH 7.4], 150 mM NaCl, 0.25% Na-deoxycholate, 1% NP40, 1 mM EDTA, 1 mM Na3VO4, 1 mM NaF, 1 mM PMSF) containing complete protease inhibitor cocktail (SIGMA), Pan-Caspase inhibitor z-Asp-2.6-dichlorobenzoyloxy-methylketone and ZVAD-fmk, normalized for total protein content (100 ug) and resolved by SDS-PAGE (12% and 15% gels). Protein quantification is performed using the Bio-Rad Protein Assay Kit (Bio-Rad). Proteins are transferred (overnight 150 mA, 4 □C) to PVDF membranes (Amersham Pharmacia). After blocking with 5% skim milk in TBST (50 mM Tris [pH 7.6], 150 mM NaCl, 0.05% Tween 20) at room temperature for 2 hours, blots are incubated overnight with antisera specific for particular IAP family members. After incubation with HRPase-conjugated secondary goat anti-rabbit (either Bio-Rad or Santa Cruz) antibody at room temperature for 1 hr, immunodetection is accomplished by an enhanced chemoluminescence (ECL) method (Amersham), with exposure to x-ray film (Kodak/XAR). Densitometry is performed to quantify the intensity of bands, using Image-pro Plus software. The immunoblotting results confirmed the immunohistochemistry observations described above.

Correlation of Protein Expression with Clinical Outcome

To analyze the relation of biomarkers with patient survival, the comparisons of the immunoscores obtained for normal prostate epithelium and prostate cancers are used to set logical cut-offs for dichotomization of data.

Clinical data are available for all patient specimens included on the tissue microarray with respect to relapse and overall survival, with a median follow-up of 5 years. Patients are categorized as: (i) Alive without disease (A); (ii) Alive with recurrent disease (R); or (iii) Dead (D). An unpaired t-test method is used for comparisons of XIAP, cIAP1, and cIAP2, and immunoscores in the A, R, and D groups of patients. P-values refer to a comparison of group A with the combined groups R and D.

To analyze the relation of biomarkers to patient survival by another method, immunostaining data for these proteins are dichotomized into high- versus low-expression groups. For this purpose, the comparisons of the immunoscores obtained for normal prostate epithelium and prostate cancers are used to set logical cut-offs for dichotomization of data. Immunoscores for normal and malignant prostate epithelium are depicted in a graphic form in FIG. 1. Based on comparisons with normal prostate epithelium, cutoffs for dichotomizing immunostaining data are selected. For example, the range of immunoscore for 95% of normal specimens can define a group of tumors with low immunoscore for IAPs. Also bimodal distribution of proteins can help to identify cut-offs for IAPs.

All biomarkers data and outcome measures are entered into a database using STATISTICA software system (StatSoft). The log rank test is used to for correlation of immunoscore data with the patient survival. The Kaplan-Meier curves illustrate correlations of the investigated biomarkers with survival for this cohort of patients.

Multivariate Cox proportional hazards models are fitted to assess whether elevated levels of biomarkers are associated with disease-free survival (DFS) and overall survival (OS). In addition, the data mining system LERS (Learning from Examples based on Rough Sets) is employed to perform a multivariate analysis of immunohistochemical staining data.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of determining a prognosis for survival for a patient with a prostate neoplastic condition, comprising:
   (a) measuring the level of XIAP, wherein XIAP comprises SEQ ID NO:2, in a neoplastic prostate tissue sample from said patient, and
   (b) comparing the level of XIAP in said sample to a reference level of XIAP in non-transformed prostate cells,
   wherein an increased level of XIAP in said sample compared to the reference level indicates a prognosis of increased survival of said patient.

2. The method of claim 1, wherein said survival is overall survival.

3. The method of claim 1, wherein said survival is longer disease-free survival.

4. The method of claim 1, wherein said measuring comprises using an antibody specifically reactive with the sequence encoded by SEQ ID NO:2 of said XIAP.

5. The method of claim 1, wherein said patient has an early stage of prostate cancer.

6. The method of claim 1, wherein said level of XIAP is used to determine the proper course of treatment for said patient.

7. The method of claim 1, further comprising measuring the level of a second biomarker in said neoplastic prostate tissue sample and comparing the level of said second biomarker in said sample to a reference level of said second biomarker in non-transformed prostate cells, wherein the relative level of said second biomarker to said reference level indicates a prognosis for survival of said patient, wherein said second biomarker is an IAP biomarker selected from the group consisting of a cIAP2 polypeptide comprising SEQ ID NO:6, a cIAP1 polypeptide comprising SEQ ID NO:4, and Survivin.

8. The method of claim 7, wherein said IAP biomarker is the cIAP1 polypeptide comprising SEQ ID NO:4.

9. The method of claim 7, wherein said IAP biomarker is the cIAP2 polypeptide comprising SEQ ID NO:6.

10. The method of claim 7, wherein said IAP biomarker is Survivin.

11. The method of claim 1, further comprising measuring the level of a second biomarker in said neoplastic prostate tissue sample and comparing the level of said second biomarker in said sample to a reference level of said second biomarker in non-transformed prostate cells, wherein the relative level of said second biomarker to said reference level indicates a prognosis for survival of said patient, wherein said second biomarker is an IAP biomarker selected from the group consisting of a cIAP2 polypeptide comprising SEQ ID NO:6 and a cIAP1 polypeptide comprising SEQ ID NO:4.

12. The method of claim 11, wherein said IAP biomarker is the cIAP2 polypeptide comprising SEQ ID NO:6.

13. The method of claim 11, wherein said IAP biomarker is the cIAP1 polypeptide comprising SEQ ID NO:4.

14. A method of determining a prognosis for survival for a patient with a prostate neoplastic condition, comprising:
 (a) measuring a level of XIAP, wherein XIAP comprises SEQ ID NO:2, in a neoplastic prostate tissue sample from said patient, and
 (b) classifying said patient as belonging to either a first or second group of patients, wherein said first group of patients having a high level of XIAP relative to a reference level in non-transformed prostate cells is classified as having a prognosis for increased survival compared to said second group of patients having a low level of XIAP relative to said reference level.

15. The method of claim 14, wherein said survival is overall survival.

16. The method of claim 14, wherein said survival is longer disease-free survival.

17. The method of claim 14, wherein said measuring comprises using an antibody specifically reactive with the sequence encoded by SEQ ID NO:2 of said XIAP.

18. The method of claim 14, wherein said patient has an early stage of prostate cancer.

* * * * *